US012594133B2

(12) United States Patent
      Habraken

(10) Patent No.:  US 12,594,133 B2
(45) Date of Patent:       Apr. 7, 2026

(54) ROBOTIC ARM

(71) Applicant: Microsure B.V., Son (NL)

(72) Inventor: Johannes Hendrikus Habraken, Vught (NL)

(73) Assignee: MICROSURE B.V., Son (NL)

( * ) Notice: Subject to any disclaimer, the term of this patent is extended or adjusted under 35 U.S.C. 154(b) by 541 days.

(21) Appl. No.: 18/146,937

(22) Filed: Dec. 27, 2022

(65) Prior Publication Data

US 2024/0206992 A1      Jun. 27, 2024

(51) Int. Cl.
     *A61B 34/30*       (2016.01)
     *A61B 34/00*       (2016.01)
(52) U.S. Cl.
     CPC .............. *A61B 34/30* (2016.02); *A61B 34/71* (2016.02); *A61B 2034/303* (2016.02); *A61B 2034/306* (2016.02)
(58) Field of Classification Search
     CPC ........ A61B 2034/303; A61B 2034/306; A61B 34/30; A61B 34/71
     See application file for complete search history.

(56) References Cited

U.S. PATENT DOCUMENTS

2014/0296872 A1 * 10/2014 Cooper .............. A61B 17/3421
                                                                606/130
2018/0056044 A1 *  3/2018 Choi ...................... A61B 34/30

* cited by examiner

*Primary Examiner* — Scott Luan
(74) *Attorney, Agent, or Firm* — McCoy Russell LLP

(57)                ABSTRACT

The disclosure relates to a robotic arm for use in surgery, microsurgery or supermicrosurgery, in particular for anastomosis, comprising: at least one instrument module comprising an instrument actuation submodule, wherein the instrument actuation submodule is configured to operate grasp and roll orientation of an instrument, wherein the instrument actuation submodule comprises a first motor and a first drivetrain for actuation of the instrument roll orientation, and wherein the instrument actuation submodule comprises a second motor and a second drivetrain for actuation of the instrument grasp orientation, at least one pitch module, and at least one yaw module.

19 Claims, 18 Drawing Sheets

146

106

106

106

106

106

306

306

106    306

306

306

106

306

306

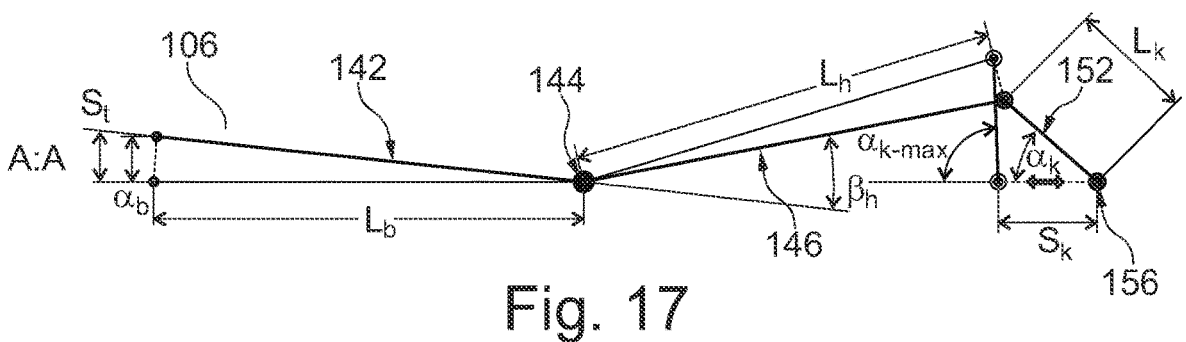
Fig. 17
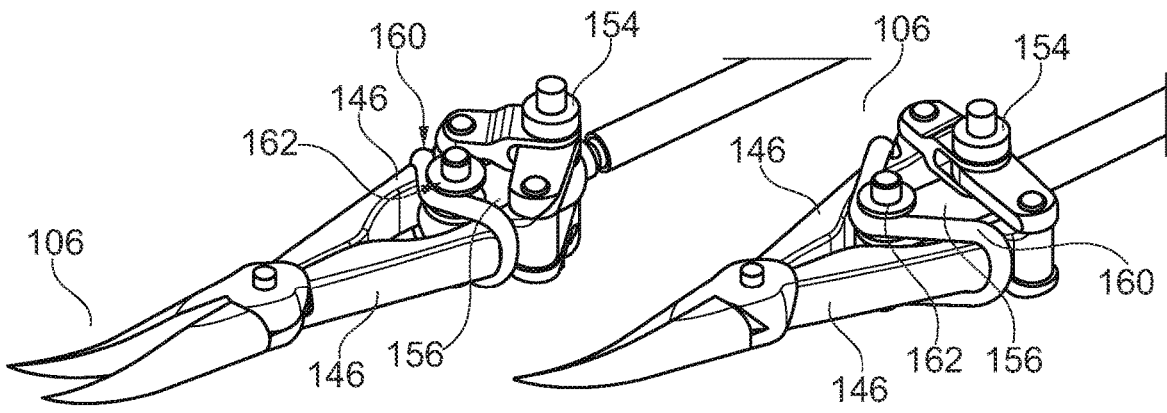
Fig. 18
Fig. 19

Excenter offset

187

$a_x$

188

136

164

158

196

194

192

194

186  188  136  190

198

188

190

187

268

SECTION A-A

270

276

278

280

254

286

304

ROBOTIC ARM

TECHNICAL FIELD

The present disclosure relates to the technical field of robotic arms and robotic systems for use in surgery, microsurgery or super-microsurgery procedures.

For instance, the robot arm or robotic system can be used in performing anastomoses.

BACKGROUND

Anastomosis in microsurgery is a technique used to (re-)connect veins, arteries, and lymphatic vessels. This allows the flow of blood or lymphatic fluid to be restored in situations such as vascular congestion, (clinical)trauma, and tissue transplantation.

Microsurgeons perform anastomoses on vessels, which range in diameter from 2.5 mm down to 0.3 mm. These vessels are primarily connected end-to-end, by up to ten interrupted sutures around the circumference of the vessel. Classically, the surgeon places each suture by hand, using fine instruments to manipulate tissue, needle, and thread. The quality of an anastomosis depends on the precision of these fine manipulations, and the overall efficiency of the procedure. Experienced microsurgeons are able to efficiently suture on the micro scale, but this requires a high level of (fine motor) skill and long-term concentration. In particular, the inherent hand tremor makes fine instrument manipulations difficult, and this limits the manual operating precision to approximately 100 μm. Alternatively, robots can be used for precise surgical handlings on the submillimeter scale.

In particular, the use of robots facilitates accurate movements with micrometer precision without substantial tremor, thereby superseding the limitations of human hand manipulation.

SUMMARY

Robots for use in surgical, microsurgical or super-microsurgical procedures are known in the art.

EP3900650A1 discloses a surgical robotic system comprising a spherical wrist comprising a surgical instrument, which allows the surgical instrument to be actuated with high accuracy. The spherical wrist comprises a yaw axis, a pitch axis, and a roll axis to provide the surgical instrument with three rotational degrees of freedom, including a roll rotation about a longitudinal axis of the surgical instrument.

Since in anastomosis sutures are placed around the circumference of each vessel, the ideal instrument orientation changes throughout the procedure. New robot concepts may therefore improve on operating efficiency by a design that focuses on achieving high instrument dexterity and convenient repositioning. Such a robot can allow a robotic assisted surgeon to operate more naturally and to assume a favorable instrument pose throughout the procedure.

Another argument for a dexterous manipulator involves the invisibility of system boundaries when operating the robot. In manual procedures, surgeons directly hold the instruments and are constantly aware of the relative position and orientation of their hands and arms through the sense of proprioception. Using robotic assistance however, this sense of awareness is lost in the translation from the master to the robot. Since surgeons only see the tips of their instruments through the microscope, it is very challenging to keep track of the changes in the manipulator's posture brought about by a sequence of instrument manipulations. Consequently, this commonly causes the surgeon to unintentionally steer the robot away from its ideal configuration, unaware of this process until the system hits a mechanical boundary. Recovery typically requires the robotic arm to be manually repositioned to its starting configuration before resuming the procedure. One approach to increase the awareness of system bounds could be the implementation of haptic feedback in the masters. However, only considering the robot, an expansion of the manipulator's dexterous workspace appears most effective in limiting the interference with system bounds.

Most microsurgical procedures require the vessels to be dissected from surrounding tissue prior to anastomosis. For some, the orientation of these vessels is often not well known in advance. As a consequence, large rotations may still be required to bring the instruments into the correct orientation for suturing after the initial setup of the robotic system. These macro-adjustments in position and orientation are typically performed manually through the repositioning of the robot's support structure. Nevertheless, a design for a robot that prioritizes dexterity and maneuverability may minimize the need for manual adjustments of the support structure during the procedure.

Thus, it is necessary that robots provide the operator (e.g., a surgeon) with sufficient dexterity, so as to be able to perform complex movements in the microsurgical workspace and also avoid the risk of collision with other objects during manipulation.

It is an object of the present disclosure to provide an alternative robotic arm for use in surgery, microsurgery or super-microsurgery, in particular for anastomosis, with enhanced precision and dexterity.

The object is solved according to the present disclosure by a robotic arm. Accordingly, a robotic arm for use in surgery, microsurgery or supermicrosurgery, in particular for anastomosis, comprising at least one instrument module comprising an instrument actuation submodule, wherein the instrument actuation submodule is configured to operate grasp and roll orientation of an instrument, wherein the instrument actuation submodule comprises a first motor and a first drivetrain for actuation of the instrument roll orientation, wherein the instrument actuation submodule comprises a second motor and a second drivetrain for actuation of the instrument grasp orientation, at least one pitch module, and at least one yaw module.

The disclosure is based on the basic idea that the robotic arm is designed to offer high dexterity and precise actuation of a surgical instrument. In particular, this is primarily achieved by the robotic arm comprising an instrument module, which in the essence serves two primary functions. On the one hand, it provides a universal interface to offer consistency in the attachment (also operation, and exchange) of various (custom) microsurgical instruments. On the other hand, the instrument actuation submodule is directly responsible for actuation of the instrument grasp operation and roll orientation, in particular as the module directly integrates the motors and drivetrains responsible for actuation of the instrument grasp operation and roll orientation. The latter serves to shift the transmission complexity for grasp and roll away from the spherical wrist mechanism. Previously, concepts for mechanical dexterous wrists were identified a bottleneck regarding instrument dexterity. In contrast, for the proposed active instrument module, these qualities can now be pursued separately for grasp and roll. Overall, a robotic arm with improved dexterity can be provided. More-over, this effectively uncouples their implementation from the remaining five manipulator degrees of freedom of the robotic arm, and hence allows a relatively independent instrument actuation submodule.

In addition, the first drivetrain of the instrument actuation submodule may be configured and arranged for infinite instrument rotation.

The at least one pitch module may be configured and arranged for actuation of instrument pitch orientation.

In particular, the pitch module may comprise a pitch drive mechanism configured and arranged to actuate instrument pitch over an angular stroke of up to 150 degrees.

The at least one yaw module may be configured and arranged for actuation of instrument yaw orientation. In particular, the yaw module may comprise an inner tube and an outer tube, wherein the outer tube is also referred to as manipulator arm.

Further, the yaw module may comprise a yaw drive mechanism configured and arranged to actuate instrument yaw over an angular stroke of up to 150 degrees.

Overall, the instrument pitch and yaw may be operated over an angular stroke of up to 150 degrees, and when operated simultaneously they allow the instrument to dex-terously orient to the workspace.

Altogether, high dexterity and precise actuation of a surgical instrument is enabled by the instrument actuation submodule and/or the pitch module and/or the yaw module.

The robotic arm may further comprise at least one instru-ment position module comprising at least three crank mod-ules, wherein at least two crank modules are each linked to at least one strut. Linking the at least two crank modules each to at least one strut may enable restriction of freedom of movement to a defined movement, thus increases accu-racy of the movement and rigidity of the robotic arm.

Three crank-modules of the instrument position module may serve to precisely control the manipulator arm, where the struts may directly control the instrument position.

Further, at least two crank modules may be linked to the same strut. In other words, at least two crank modules may be linked to one strut only. This structure can help define the motion and allows for a simple parallel kinematic structure.

In particular, the robotic arm may be a seven degree of freedom robotic arm, wherein the instrument actuation sub-module may be a three degree of freedom module, the instrument submodule may be a one degree of freedom module and the instrument position module may be a three degree of freedom module. Thus, compared to a six degree of freedom robotic arm the end-effector pose can not only be reachable in a single configuration of the robotic arm.

Three degrees of freedom may correspond to the posi-tioning of the instrument and arm in space. To this end, a parallel kinematic structure may be employed that is con-structed. Here, the actuators may be mounted at the base of the robotic arm to reduce moving mass, with their drive stiffnesses acting in parallel rather than stacked in series. Two of the parallel linkages may be slender struts that attach to the tip of the manipulator arm. Each of these struts may be controlled by a direct drive balanced crank mechanism that prescribes one of the three actuated degrees of freedom at the manipulator arm. A similar crank mechanism may directly act on the rear of the arm and therein controls the third and last positioning degree of freedom. In addition, this latter crank constrains the remaining three passive degrees of freedom for the manipulator arm such that both its position and orientation in space may be fully defined.

In general, the robotic arm may comprise at least one parallel kinematic structure being formed by at least one of an instrument module and/or a yaw module and/or a pitch module and/or an instrument position module. Overall, this may enable high structural stiffness of the robotic arm.

The instrument module may be characterized by a modu-lar structure. In other words, the instrument module may comprise at least one of a (sub-)module, an element, a joint, a drivetrains, a motor, etc.—all of which again my comprise several single elements. In particular, the instrument module may, in addition to the instrument actuation submodule, comprise an instrument submodule, wherein the instrument submodule may comprise an instrument retainer and an instrument. In other words, the instrument submodule may comprise a microsurgical instrument integrated into a matched retainer body.

The instrument may be a needle holder and/or forceps for surgery, microsurgery or supermicrosurgery, in particular for anastomosis, comprising two instrument beaks, at least one instrument hinge pin, at least two instrument handles and at least two handle joints.

In particular, the instrument may have length of less than 50 mm, in particular less than 30 mm, in particular 20 mm. Conventional traditional instruments, such as a traditional needle holder, have a length of about 150 mm. Thus, a sharp reduction in instrument length compared to the typical 150 mm for a traditional instrument/needle holder is achieved. This allows the instrument to be better suited for integration into the robot device, in particular the instrument retainer. Also, compared to conventional instruments for other robotic arms, the present instrument is more compact, with a length of approximately two thirds of the size of conven-tional instruments for robotic arms. In addition, the use of more compact instruments is motivated by the intended application of the robot in the upper range of precision procedures, such as anastomosis. Here, manipulations involve increasingly delicate tissue and sutures that pair well with the use of refined, compact instruments.

In particular, the beaks each may have a length of less than 20 mm, in particular less than 15 mm, in particular 10 mm. This dimension corresponds to the downscaling of the instrument to approximately two thirds of the size of con-ventional instruments for robotic arms. From a mechanical point of view, a reduced beak length serves to proportionally limit the maximum output arm for grasp. In turn, this again proportionally enables reduction of the required amount of force applied at the handle to clamp a needle with a force of e.g. over 5 N at the beaks. In addition, the use of compact instruments is motivated by the intended application of the robotic arm in the upper range of precision procedures. Here, manipulations involve increasingly delicate tissue and sutures that pair well with the use of refined instruments. Moreover, fine beaks appear less bulky at the enhanced levels of microscopic magnification that may be employed for a robotically steadied instrument.

Consequently, type-specific instrument functionality ema-nates predominantly from the beaks. These may be designed to preserve the shape of their traditional counterparts, which are already tailored to the microsurgical procedure. More-over, this close correspondence in design may aim to facili-tate the surgeon's transfer of skill from manual to robotic assisted surgery. Similar to their traditional counterparts, the custom instruments may be designed to be produced from surgical e.g. grade stainless steel, although e.g. titanium variants may be considered as well.

In particular, the instrument may be configured and arranged for an inverted hinge mechanism. Consequently, the beaks close instead of open upon the spreading of the instrument handles. This inversion serves the implementation of a knee mechanism for actuation of the instrument. The knee-mechanism is characterized by a non-linear input/output relation (linear input stroke at the knee, output at the instrument beaks). The non-linearity of the knee-mechanism serves in the design of the instrument module to increase the grasp clamping force and precision the further the beaks close. This allows the actuator effort for grasp to be concentrated where it matters most.

Therefore, the instrument retainer may comprise at least one knee mechanism central joint, at least two retainer guide pins, at least one stopper, at least one knee link pair, wherein the instrument retainer is configured to actuate the instrument by an inverted hinge mechanism. Overall, this enables a non-linear input/output relation (linear input stroke at the knee, output at the instrument beaks), as described above.

Further, the instrument actuation submodule may comprise a pushrod configured and arranged for actuating over the centerline of the instrument actuation submodule. The knee mechanism described above is in part selected for its short linear input stroke for grasp. Such motion may be convenient in the construction of a sterile barrier. In addition, this actuation stroke can be aligned along the roll centerline. This allows the operation of grasp to be conveyed independent from the instrument roll orientation. To this end, a pushrod is introduced, which acts over the centerline of the instrument actuation submodule. Moreover, a direct contact between this pushrod and the knee mechanism central joint serves to link the input motion at the drive to the operation of the beaks at the output. In particular, the pushrod may comprise a spherical tip configured for contacting a matching socket in the knee mechanism central joint.

Further, the instrument retainer may comprise at least one instrument preload band and at least one preload band guide pulley. This contributes to enabling a non-linear input/output relation (linear input stroke at the knee, output at the instrument beaks), as described above. In particular, the preload band is applied to both the instrument handle and the knee mechanism central joint, maintains the contact between pushrod and knee mechanism central joint and serves to remove play from the assembly. In particular, the instrument preload band is guided by the preload band guide pulley located on the knee-mechanism central joint as the band is applied at the handles and tensions them together, the preload force will always act through the links of the knee mechanism. Consequently, the joints of the knees are always in contact in the direction corresponding to a closing action, such that no play is traversed upon the clamping of an object.

The preload band may be produced from an elastomer, in particular an autoclave compatible elastomer, such as AFLAS.

Neither bacteria, nor viruses or spores should be transferred from the robotic system to the patient. To this end, parts of the robot may be covered by a physical sterile barrier impermeable to contaminants, such as a disposable drape, Drapes may be made application specific, produced in the required shape by bonding plastic sheets in a pattern. Moreover, physical components of different material may be incorporated in the sheets at an increase in complexity and cost. Although drapes are relatively flexible and strong, they remain vulnerable to mechanical contact stresses, which can cause punctures or tear the material. The drape should be kept clear from the microscope's and surgeon's field of view. Since surgical instruments come into direct contact with the patient they are themselves not suitable for draping.

Therefore, these and any critical components outside the sterile barrier should be either cleanable and sterilizable, or be single use disposable. Sterilization is the process of destroying or inactivating the bacteria, viruses, and spores on critical components. It is preceded by cleaning, during which organic residue such as blood is removed. Autoclave pressurized steam-sterilization is the most common and cost-effective method that is available in all hospitals. This procedure is efficient, and as an indication takes a minimal of 4 minutes at 132° C. in a pre-vacuum sterilizer, or 30 minutes at 121° C. in a gravity displacement autoclave.

Components designed for autoclave sterilization must be heat tolerant, corrosion resistant, and non-absorbing. Moreover, cleaning and sterilization are generally facilitated by good exposure and smooth surfaces, without cavities or blind holes.

The robotic arm is characterized by a modular structure. The at least one instrument module, the at least one pitch module, the at least one yaw module as well as the instrument position module each comprise several elements or modules (such as a drivetrain and/or a joint—each again comprising several elements). The robotic arm may be designed sterilizable for all the joints and drivetrains regarding the orienting degrees of freedom and instrument grasp. In other words, the modular structure of the instrument module, and/or the pitch module and/or the yaw module and/or the crank module may be configured sterilizable for all the joints and drivetrains regarding the orienting degrees of freedom and instrument grasp. In particular, the instrument module (instrument actuation submodule and instrument submodule) and/or the pitch module and/or the yaw module and/or the crank module may comprise joints and/or elements for orienting the instrument and/or instrument grasp, wherein these joints and/or elements are configured sterilizable. In other words, parts of the instrument module, and/or the pitch module and/or the yaw module and/or the crank module may be configured for sterilization (in particular autoclave sterilization). This serves for minimal drape interference on instrument reorienting.

Overall, as described above, sterilizable elements and/or joints enable operation under sterile conditions, avoiding transfer of infectious microorganisms (such as bacteria, viruses, spores (of fungi) to the patient. In addition, single sterilizable elements of the robotic arm may enable the interchange of instrumentation during surgery. Afterwards, separation of parts serves once more to increase the exposure of inner surfaces for the process of cleaning and sterilization.

For efficiency in cleaning and sterilization the robotic arm may be designed to easily disassemble and thereby improves exposure of the submodule surfaces.

Medical robotics are subject to strict safety regulations, especially when they operate in direct contact with the patient. In case of the robotic arm, the focus must therefore always be on a safe and robust design that minimizes any risk to the patient and medical personnel. To this end, the following set of operational requirements is imposed on the robotic arm:

The robot must be sterile in surgery (see above).

The movement speed at the instrument tip is limited to 10 $mms^{-1}$.

The rotational velocity of the instrument is limited to $\pi/2$ rad $s^{-1}$.

Accelerations shall be low.

The exerted force at the tip of the instrument may not exceed 5 N.

The supply voltage is limited to 24V.

These requirements help limit the robotic arms potential to do damage. In addition to these operational safety requirements, the risks associated to abnormal conditions must be evaluated as well. These include events such as an unexpected power shutdown, or the failing of one or more components. Mechanical safety features may include inherent force limitation, back-drive-ability, redundancy in sensors, and weight compensation of the slave manipulator.

Inherent force limitation serves to limit the potential of the system to do harm in operation. To this end, actuators and control system in the slave may be no more powerful than required to produce a force of 0.5 N at the instrument tip.

Back-drive-ability allows the robotic system to be repositioned manually in case of a fault. This allows the robot to be cleared quickly away from the operating site in case of a hazardous situation, or when manual access is required. The yaw orientation and instrument position may be fully back-drivable to allow manual repositioning upon fault or convenience.

Redundancy in sensors serves to detect faults in the system by providing redundant measurement data for read-out comparison. Upon the detection of a fault, the system may assume a safe state rather than that the controller continuous to drive the system based on an erroneous feedback signal. All but the grasp and roll drive may integrate a redundant pair of absolute position sensors for fault detection. These may also serve to provide instantaneous awareness of the robotic arm configuration on startup without requiring a homing procedure. In contrast, for grasp and roll no position sensors may be implemented as these drives are argued safe in open-loop control.

Weight compensation serves to balance the mechanical links of the robotic arm around the respective joints. This allows the arm to continuously operate in an equilibrium, such that upon fault (e.g. loss of power) the arm does not collapse on the patient. Moreover, a balanced arm requires minimal continuous actuator effort to maintain any given posture. In particular, the strut cranks may be balanced such that the arm/system does not collapse on loss of power.

The present disclosure further relates to a robotic system for use in surgery, microsurgery or supermicrosurgery, in particular anastomosis, comprising at least two robotic arms as described above. This enables performing complex surgeries requiring more than one robotic arm characterized by high dexterity.

Further details of the disclosure shall now be explained with reference to an example embodiment shown in more detail in the drawings.

BRIEF DESCRIPTION OF THE DRAWINGS

It is shown in

FIG. 4: an example of the procedure for microsurgical anastomosis, pulling the needle and suture-head through;

FIG. 17: an illustration of the dimensioning of the knee mechanism;

FIG. 18: an illustration of the instrument knee mechanism—preloading;

FIG. 19: an illustration of the instrument retainer holding the instrument;

DETAILED DESCRIPTION

Figures 1, 2, 3:
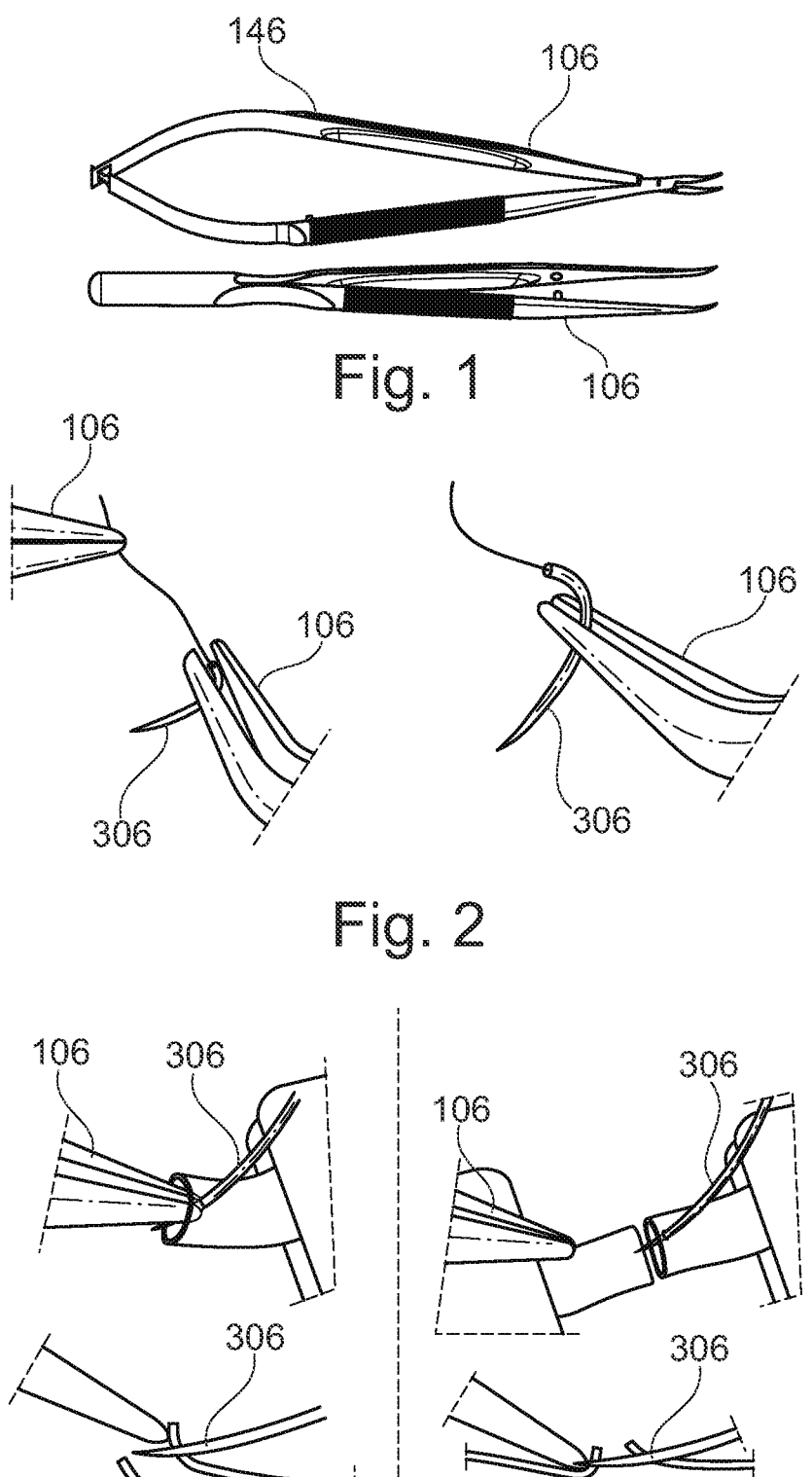
FIG. 1: classical Microsurgical instruments (needle holder and forceps)
FIG. 2: an example of the procedure for microsurgical anastomosis, picking-up the needle.
FIG. 3: an example of the procedure for microsurgical anastomosis, entry bite and exit bite.

FIG. 1 shows a needle holder 106 and forceps 106 as predominantly used by microsurgeons, to perform precision manipulations.

The needle holder 106 is shown on top of FIG. 1, whereas the forceps 106 are shown on the bottom of FIG. 1.

Both needle holder 106 and forceps 106 represent traditional surgical instruments 106.

The needle holder 106 is the main instrument 106 for suturing, which holds the needle 306 while making the entry and exit bites.

It has a hinge approximately 15 mm from the tip, such that the instrument handle 146 acts as a lever. This allows the surgeon to firmly secure the needle in the beaks, exerting over 5 N of clamping force to prevent slippage.

FIGS. 2-5 together show an example of the procedure for microsurgical anastomosis.

An anastomosis starts with two vessels, surgically prepared to be (re-)connected by sutures.

Their vessel-ends are positioned and held relative each other in vascular clamps. The main suturing techniques for anastomosis are described below. They are primarily based on Acland's practice manual for microvascular surgery. Some of the corresponding illustrations are included to visualize the procedural steps.

FIG. 2 illustrates an example of picking-up the needle 306: the needle 306 is grabbed with the needle holder 106, just above half-height. It is oriented at a right angle to its beak, aided by the forceps 106 and the at sides on the base of the needle 306.

FIG. 3 shows an example of the entry-bite (left site). The entry-bite is made such that the needle 306 punctures the vessel wall from the outside inwards. The forceps 106 are used simultaneously to push the edge of the vessel wall from the inside up. This allows the needle 306 to puncture approximately perpendicular to the vessel wall, while minimizing the risk of a through-stitch. FIG. 3 also shows an example of the exit-bite (right site). The exit-bite is subsequently made on the opposite vessel-end. Again, the forceps 106 are used to restrain the vessel and to curl its edge up for a perpendicular puncture, now from the inside out.

Figure 4:
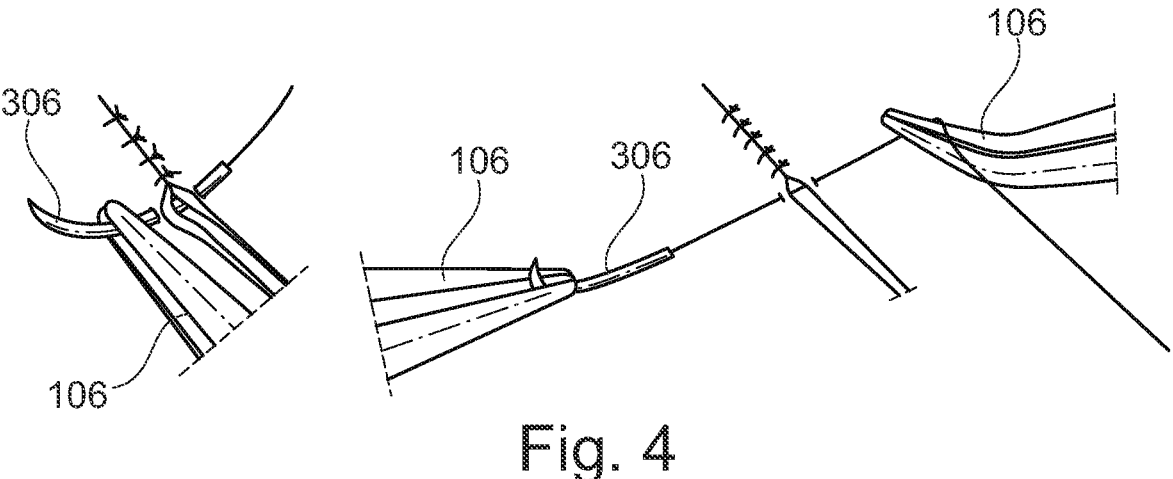

FIG. 4 shows an example of pulling the needle 306 and suture-thread through. The needle-tip, now protruding from the vessel wall, is grabbed by the forceps 106 and pulled through. Subsequently, the suture-thread is pulled along with the needle 306, guided over the beaks of the needle holder to minimize stress on the vessel wall near the entry bite. Depending on the remaining suture-length, the needle 306 is dropped and the thread is grabbed and pulled through in multiple steps. This allows the manipulation to be performed within the microscope's limited field of view. However, care must be taken to preserve the integrity and tensile strength of the suture-thread. To this end, the suture should be clamped no more often than necessary, and may use only the forceps 106 instead of the needle holder 106.

Figure 5:
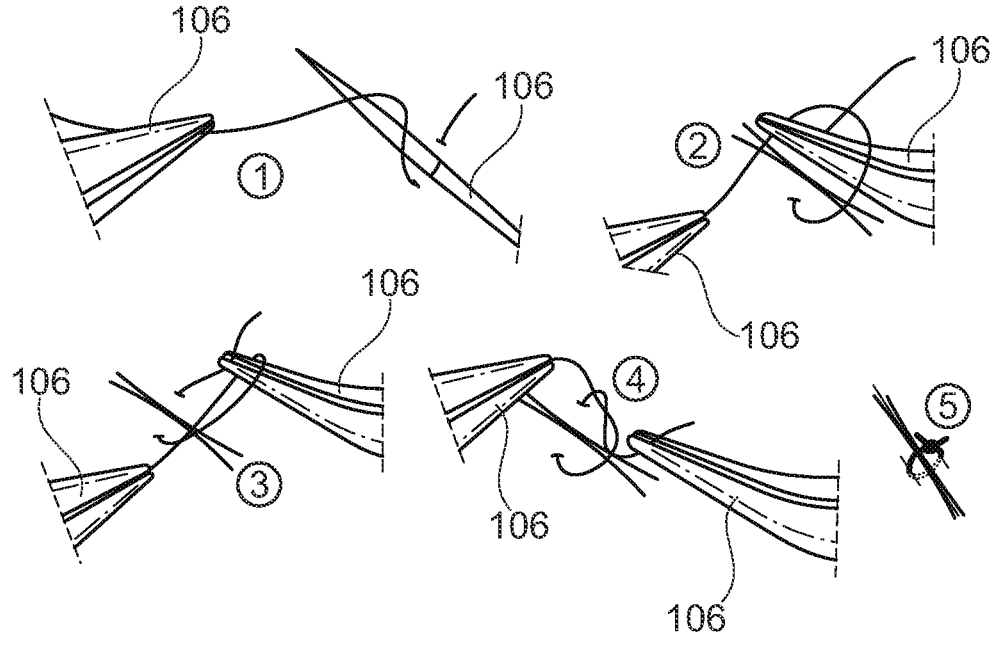
FIG. 5: an example of the procedure for microsurgical anastomosis, making the knot.

FIG. 5 shows an example of making the knot: three to four consecutive half-knots are tied to tension and secure the suture. A half-knot is initiated by grabbing the needle-side of the suture-thread with the forceps 106, and wrapping a loop around the (spread) beaks of the needle holder 106. Then, the needle holder 106 grabs the free end of the suture and pulls it back through the loop to form a half-knot. The surgeon tensions each half-knot by moving the instruments 106 apart, gently pulling on both ends of the suture-thread. The tension of the half-knot is assessed visually, as the forces involved are too small for humans to sense directly. FIG. 5 also shows an example of a cut suture-thread: The assistant cuts the suture-thread close to the knot using a micro-scissor. The remaining free ends of the knot are trimmed short and removed from the site. The result is a compact interrupted suture, that remains in place to be encapsulated in the patient's tissue.

The above steps disclosed in FIGS. 2-5 are repeated for each interrupted suture around the circumference of the vessel. The remaining length of the suture-thread decreases with each suture, but it is generally sufficient for one anastomosis.

The procedure and instruments 106 for robotic assisted anastomosis are similar to those for manual surgery as outlined above in FIGS. 2-5. This close correspondence helps trained surgeons transfer their skills and techniques from manual to robotic assisted surgery.

Most manipulations in the procedure as shown in FIGS. 2-5 require the simultaneous use of both needle-holder 106 and forceps 106. Therefore, the robot (also referred to as robotic system) features two robotic arms 100, each operating one instrument 106 (cf. FIG. 9). Through the masters, the surgeon controls both robotic arms 100 to co-operate within a shared workspace containing the vessel-ends.

Figures 6, 7:
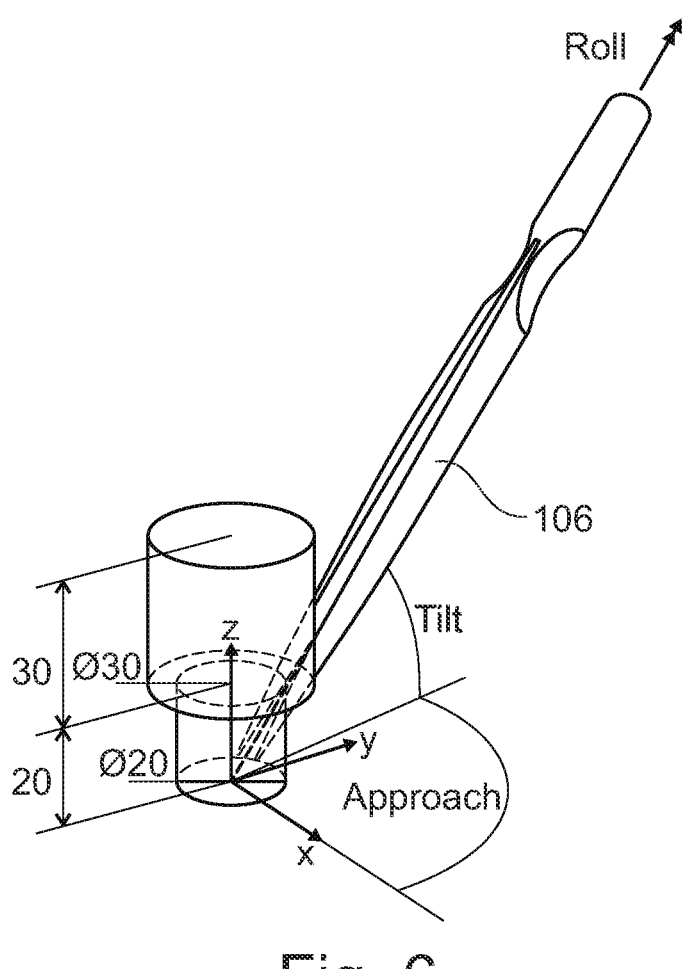
FIG. 6: an illustration of the shared workspace for anastomosis, illustrated with a traditional microsurgical forceps.
FIG. 7: an example of traditional instrument grip for manual surgery.

This shared workspace is visualized in FIG. 6, and can be subdivided into two segments.

Fine manipulations, such as making the needle 306 entry and exit bites, are done within a cylindrical volume of 20 mm in both diameter and height (first segment, referred to as precision workspace, represented by the lower cylinder with 20 mm diameter). Pulling the suture thread through and tying knots requires less precision, and a larger workspace can be utilized for efficiency. To this end, an additional cylindrical workspace is defined for suture handling (second segment, referred to as suture handling workspace). This volume has a diameter and height of 30 mm, and is stacked on top of the precision workspace. It is argued that further extensions to the workspace become less effective, as the surgeon must rely on visual feedback from the microscope to operate the instruments 106. Here, the high level of microscopic zoom proportionally limits the field of view in radial direction, while the focal range is the limiting factor in axial direction.

For future reference, a fixed Cartesian coordinate frame is defined at the base of the workspace, where the z axis is assumed to coincides with the microscope's optical axis. Furthermore, roll indicates the instrument 106 rotation about its longitudinal axis, tilt the instrument angle with respect to the x-y plane, and approach its angular position around z, with respect to the x axis.

FIG. 7 shows de traditional instrument 106 grip on the forceps 106 (left) and needle holder 106 (right) during surgery. The arrows indicate the contact points through which the surgeon manually positions and actuates the instruments 106. The grip is close to the tip for direct control, while the instrument 106 gains stability from the support point(s) at the back of the handle. Resting his hands either on the support table or directly on the patient, the surgeon can precisely position the instrument 106, and attenuate tremor to some degree. Besides grasp, the maximum required force at the instrument tip is 0.5 N associated to the tensioning of a knot. This value is based on the suture breaking force. Moreover, it is assumed that the duration of this peak force is relatively short compared to the occurrence and interval of tightening consecutive half-knots.

Figure 8:
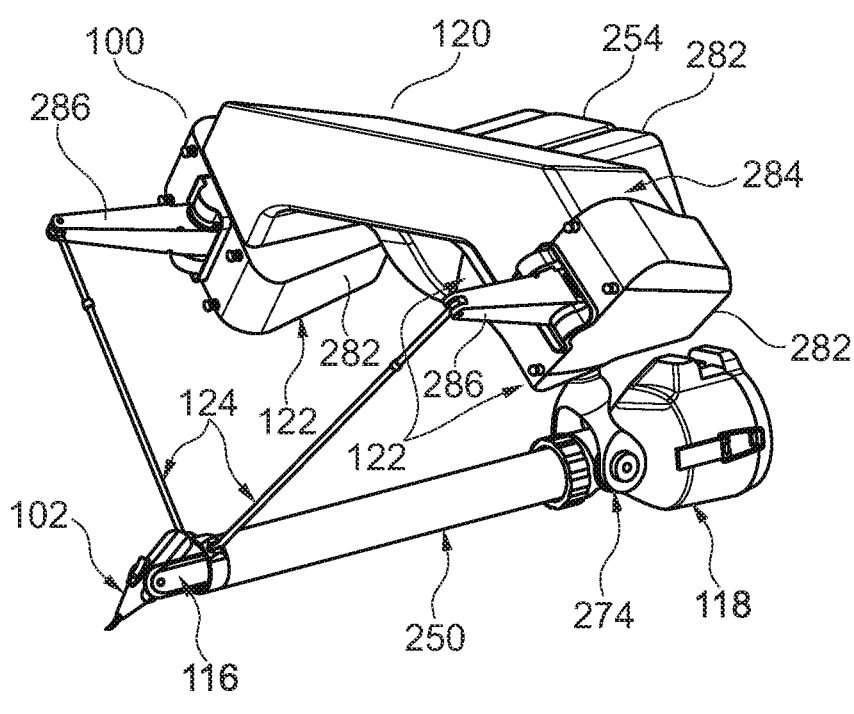
FIG. 8: an embodiment of the robotic arm according to the present disclosure.

FIG. 8 illustrates an embodiment of the robotic arm 100 according to the present disclosure.

The robotic arm 100 is configured for use in surgery, microsurgery or supermicrosurgery, in particular for anastomosis.

In this embodiment, the robotic arm 100 comprises an instrument module 102 (cf. e.g. FIGS. 11-13) comprising an instrument actuation submodule 104.

The instrument actuation submodule 104 is configured to operate grasp and roll orientation of an instrument 106.

Not show in this embodiment is, that the instrument actuation submodule 104 comprises a first motor 108 and a first drivetrain 110 for actuation of the instrument roll orientation.

Also not shown in this embodiment is that the instrument actuation submodule 104 comprises a second motor 112 and a second drivetrain 114 for actuation of the instrument grasp orientation.

Figure 24:
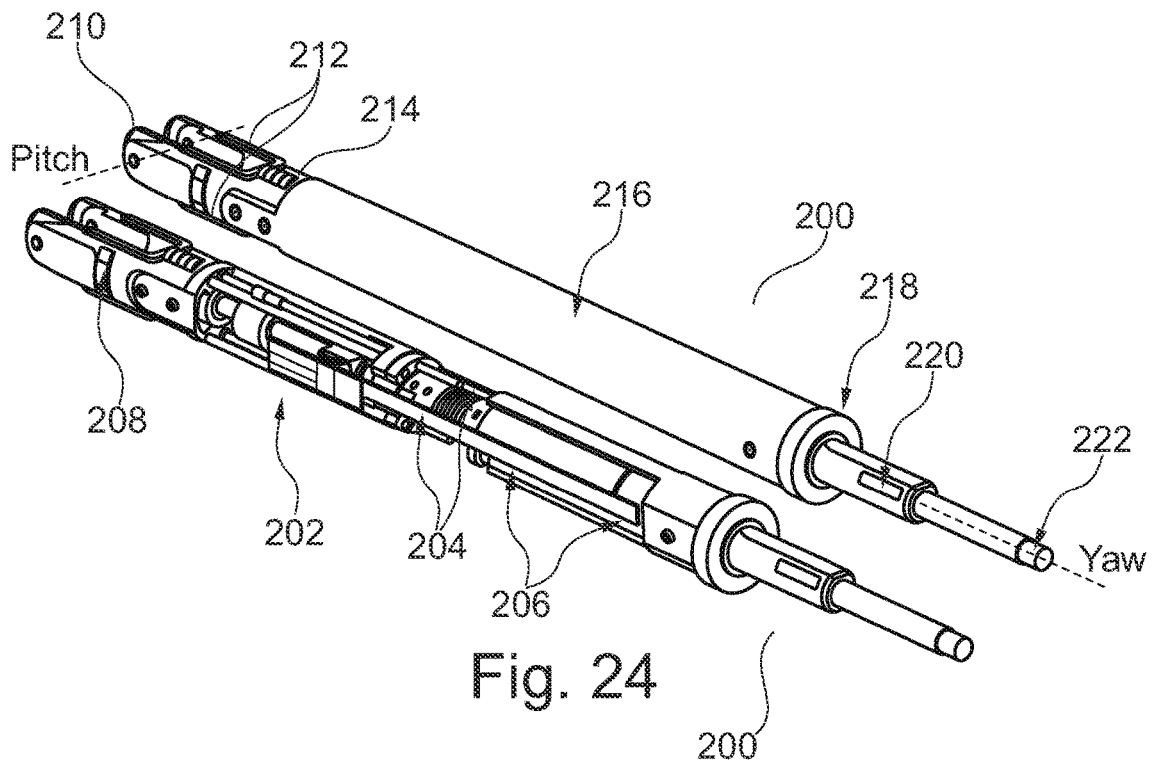
FIG. 24: an illustration of the pitch module.
Figure 25:
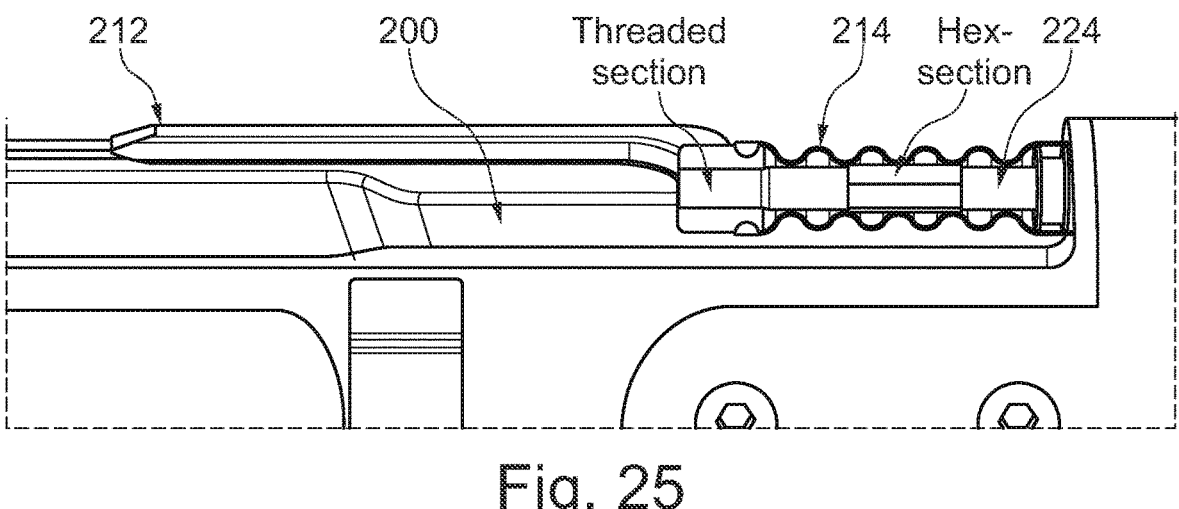
FIG. 25: an illustration of the pull member and bellow type compliant seal.
Figure 26:
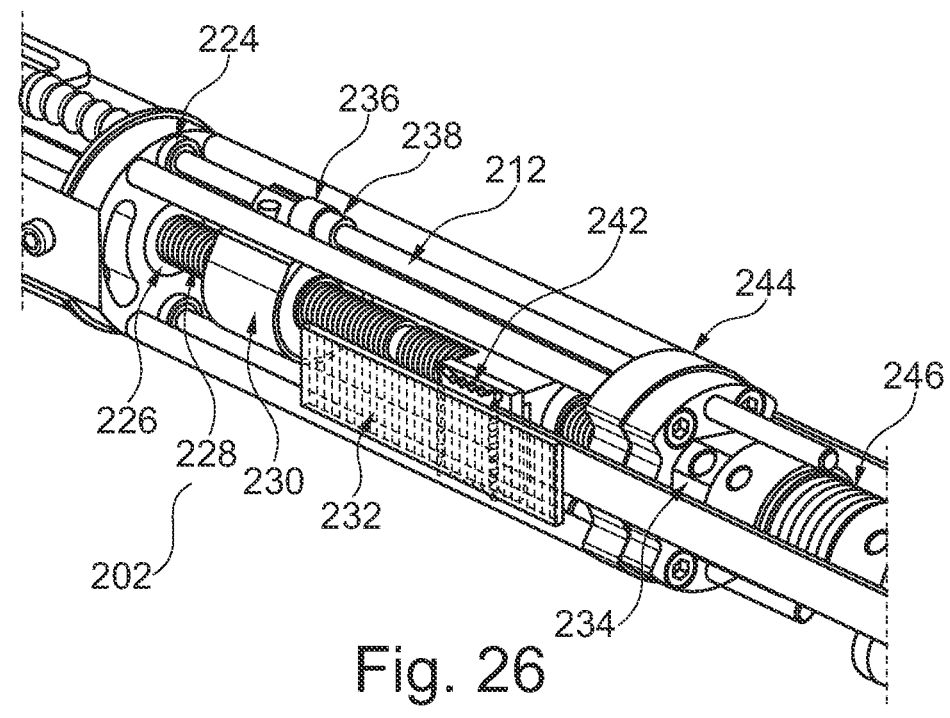
FIG. 26: an illustration of the pitch drive mechanism.

Further, the robotic arm 100 comprises a pitch module 116 (cf. FIGS. 24-26).

Still further, the robotic arm 100 comprises a yaw module 118 (cf. FIGS. 27-32).

In this embodiment, the robotic arm further comprises an instrument position module 120 (cf. FIGS. 33-36).

In this embodiment, the instrument position module 120 comprises three crank modules 122, 254 wherein two crank modules 122 are each linked to at least one strut 124.

In this embodiment, the crank module 254 not linked to a strut 124 is referred to as central crank module 254.

Alternatively, at least two crank modules 122 could be linked to the same strut 124.

Not explicitly shown in this embodiment is, that the robotic arm 100 could be arranged without an instrument position module 120.

Not explicitly shown in this embodiment is that the first drivetrain 110 of the instrument actuation submodule 104 is configured and arranged for infinite instrument 106 rotation.

Further not explicitly shown in this embodiment is that the pitch module 116 comprises a pitch drive mechanism 202 configured and arranged to actuate instrument 106 pitch over an angular stroke of up to 150 degrees, cf. FIG. 26.

Figure 38:
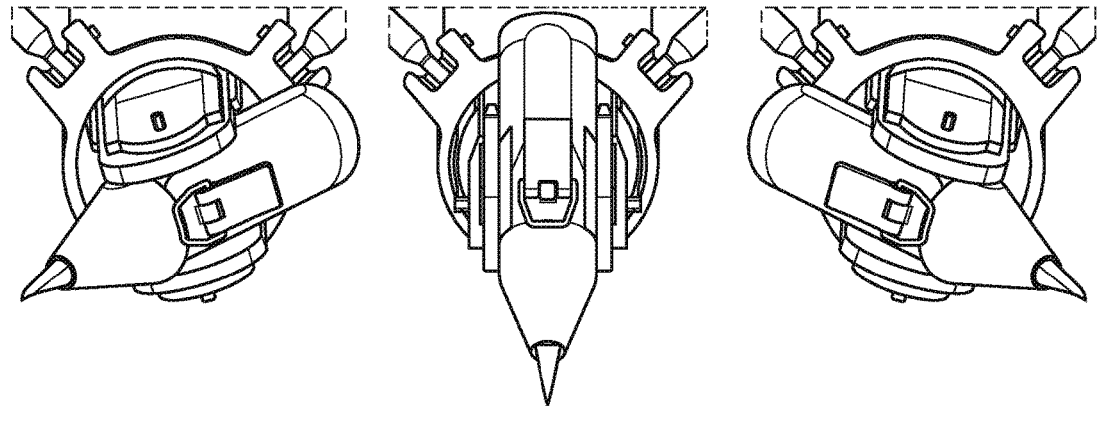
FIG. 38: an illustration of the extreme orientation of the yaw axis.

Further not explicitly shown in this embodiment is that the yaw module 118 comprises a yaw drive mechanism configured and arranged to actuate instrument 106 yaw over an angular stroke of up to 150 degrees, cf. FIG. 38.

Still further not explicitly shown in this embodiment is, that the instrument module 102 comprises an instrument submodule 126, the instrument submodule 126 comprising an instrument retainer 138 and the instrument 106, cf. FIG. 19.

In this embodiment, the robotic arm 100 is a seven degree of freedom robotic arm 100.

In this embodiment, the instrument actuation submodule 104 is a three degree of freedom module and the instrument submodule is a one degree of freedom module.

In this embodiment, the robotic arm may comprise a parallel kinematic structure being formed by the instrument position module.

In general, the robotic arm can comprise at least one parallel kinematic structure being formed by at least one of an instrument module and/or a yaw module and/or a pitch module and/or an instrument position module.

In this embodiment, the instrument position module 120 is a three degree of freedom module.

Figure 9:
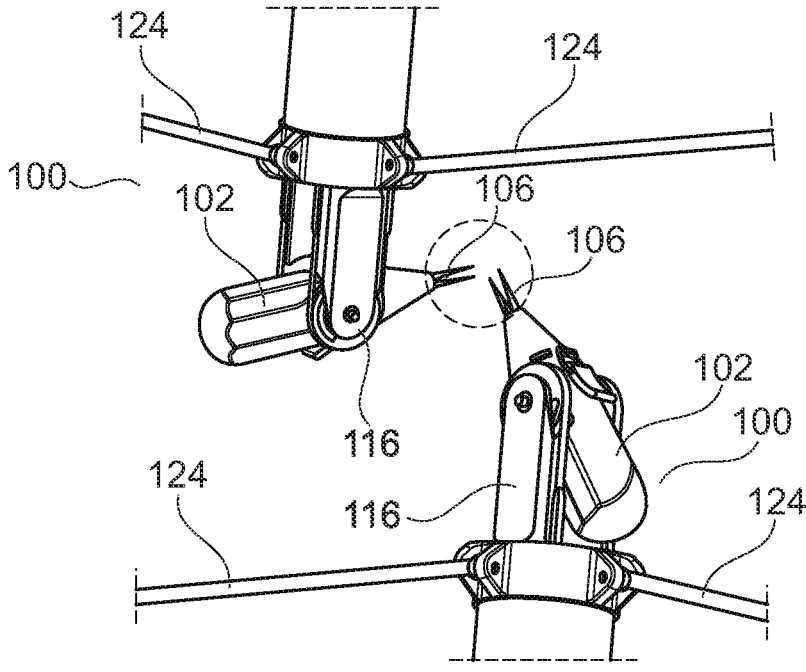
FIG. 9: an illustration of a pair of robotic arms according to the present disclosure, cooperating in a shared work space.

Not explicitly shown is, that a robotic system according to the disclosure can comprise at least two robotic arms 100 as shown in FIG. 9.

FIG. 9 shows an illustration of a robotic system comprising a pair of robotic arms 100 according to the present disclosure (as shown in FIG. 8), cooperating in a shared work space.

The robotic arm geometry is designed to efficiently perform cooperative manipulations in the workspace for microsurgical anastomosis, cf. FIG. 6.

A pair of robotic arms 100 (i.e. a robotic system comprising two robotic arms 100) cooperating in this workspace from a top-view is illustrated, with an indication of the microscope's field of view on the anastomosis. The visualized configuration serves as an example that indicates how a dexterous robotic arm 100 allows the pair of instruments 106 to assume a wide range of orientations relative to the operating site.

Figure 10:
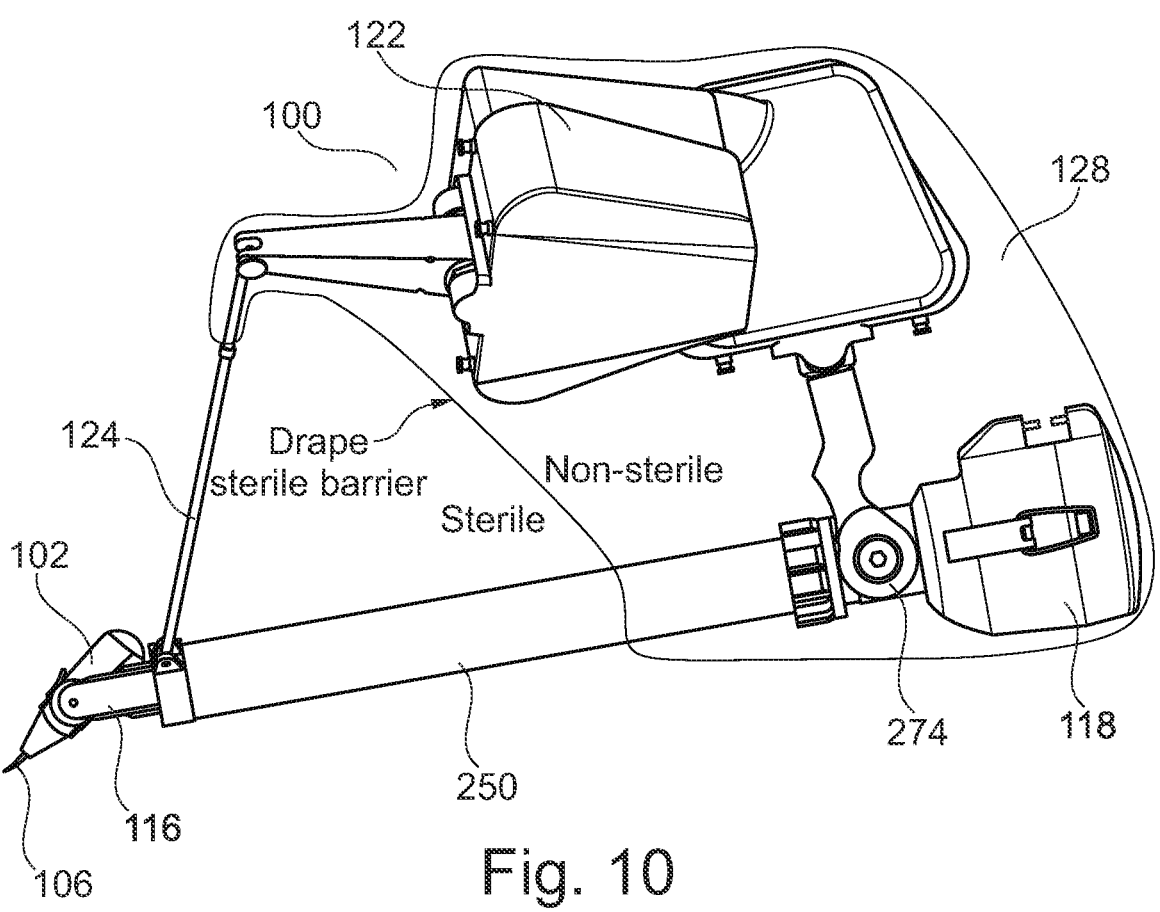
FIG. 10: an illustration of the robotic arms draped volume, and its sterilizable components.
Figure 37:
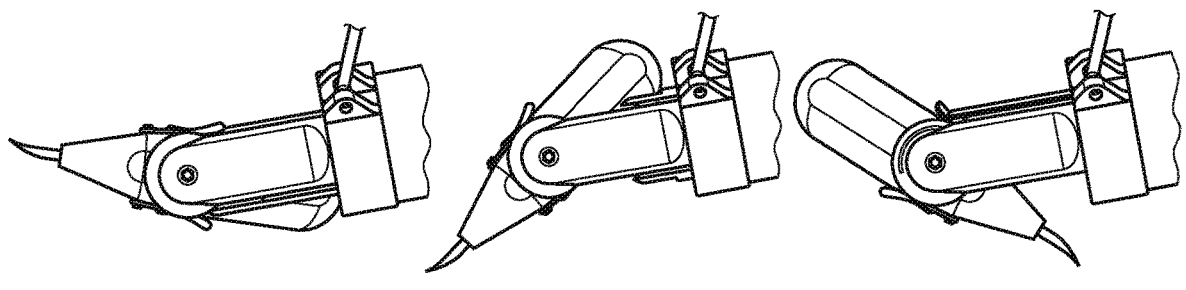
FIG. 37: an illustration of the extreme orientations of the pitch axis.

High instrument dexterity, cf. FIGS. 37 and 38. allows a more optimal orientation to be assumed for each manipulation at the benefit of the quality and efficiency of the operation, FIG. 10 visualizes the robotic arm's 100 draped volume, and its sterilizable components.

Part of the robotic arm 100 may be draped, while other components remain exposed and hence are required sterile. FIG. 10 serves to distinguish between these two by visualizing the location of the drape 128 for the concept design.

Here, the drape 128 is applied away from the instrument 106 such that it poses minimal interference with the surgeon's line of sight and manual workspace. Those parts protruding outside the drape 128 are subject to autoclave steam sterilization.

Hence, it is apparent from FIG. 10 that a substantial part of the robotic arm 100 must be designed suitable for sterilization. The added complexity of sterilizable modules is to be offset by an increase in instrument dexterity and precision.

Moreover, with sterilizable joints for grasp, roll, pitch, and yaw, none of these axes is affected by the disturbances or motion constraints typically imposed by the drape 128.

Figure 11:
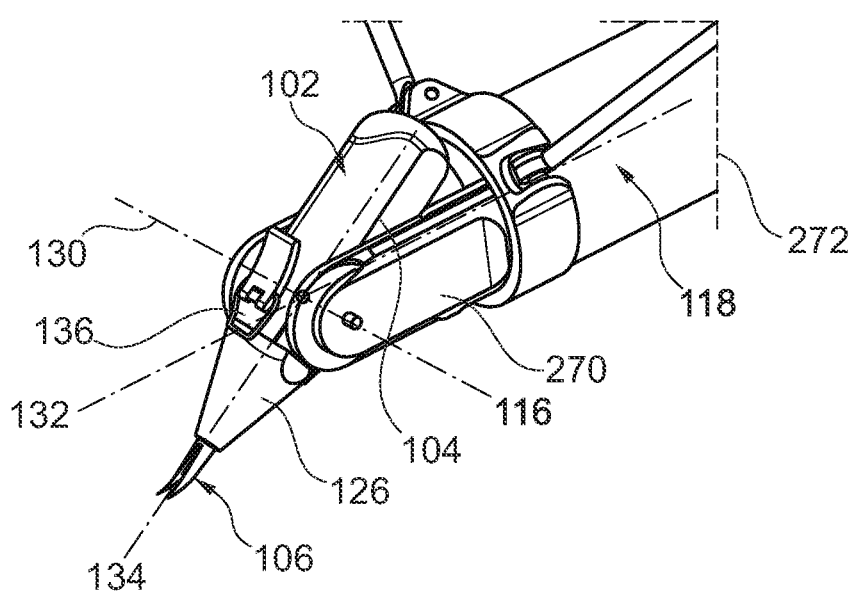
FIG. 11: an embodiment of the instrument module according to the present disclosure.

FIG. 11 shows a first embodiment of the instrument module 102 with an instrument 106, the pitch module 116 and the yaw module 118, according to the present disclosure.

The instrument module 102 hinges directly on the yaw shaft 270, for which the resulting hinge-line perpendicular to the shaft constitutes the pitch axis 130. In addition, both the drivetrain and actuator for pitch are directly integrated into this yaw shaft as well (cf. FIG. 24). The yaw orientation is imposed on the instrument 106 by a direct drive that controls the angular position of the shaft with respect to the concentric outer tube 272. This outer tube 272 in turn constitutes the manipulator arm, which serves to position the assembly of revolute joints in space.

Also shown in FIG. 11 are the yaw axis 132 and the roll axis 134.

Figure 12:
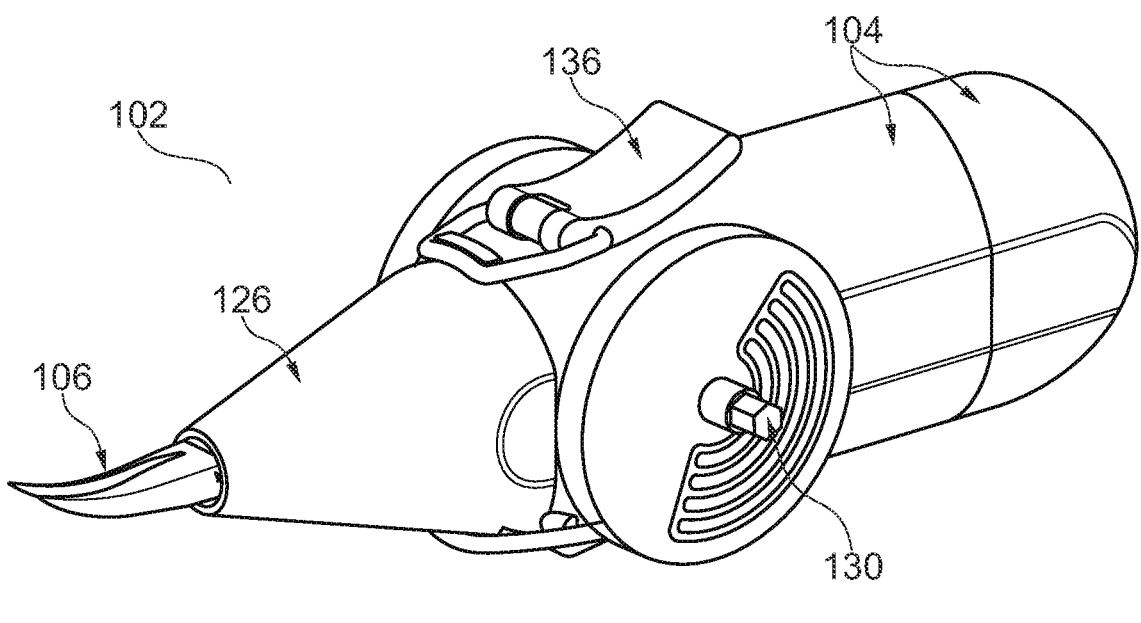
FIG. 12: a further illustration of an embodiment of the instrument module.

FIG. 12 illustrates further an embodiment of the instrument module 102 according to the disclosure, holding an instrument 106.

The instrument module 102 comprises an instrument actuation submodule 104.

Further, the instrument module 102 comprises an instrument submodule 126.

The instrument actuation submodule 104 may be understood as active part of the instrument module 102, configured for actuation of instrument 106 grasp and roll.

The instrument submodule 126 may be understood as passive part of the instrument module 102, configured for holding the instrument 106.

Shown is also the pitch axis 130.

The instrument module 102 is designed separable.

Shown are quick-lock clips 136.

Figure 13:
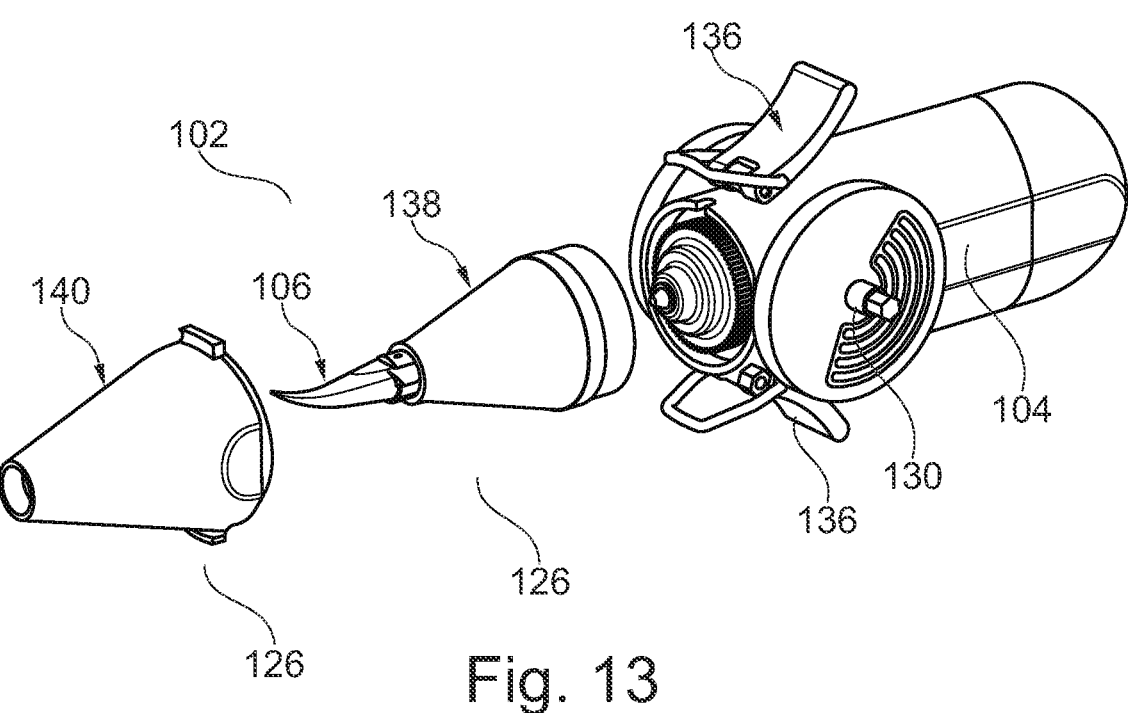
FIG. 13: a further illustration of the instrument module (disassembled status)

Disassembly of the instrument module 102 can be performed manually through the release of the quick-lock clips 136, cf. FIG. 13.

FIG. 13 shows a further illustration of the instrument module 102 (disassembled status).

Shown is the instrument submodule 126 and the instrument actuation submodule 104, which are both part of the instrument module 102.

The instrument submodule 126 comprises an instrument retainer 138 and an instrument 106.

In this embodiment, the instrument submodule 126 further comprises a retainer shell 140.

In this embodiment, the instrument retainer 138 holds the instrument 106.

In particular, the inside of the instrument retainer 138 is shaped to hold the instrument 106, cf. FIG. 19.

Also, in this embodiment, the instrument actuation submodule 102 is configured for to operate grasp and roll orientation of the instrument 106.

Further shown are the (two released) quick lock clips 136.

Not explicitly shown in FIG. 13 is that the instrument actuation submodule 102 may remain connected to the yaw shaft 270, such that the pitch transmission and electrical connections need not be detached.

The passive instrument submodule 126 in contrast features no such connections, and may therefore be swapped out freely for different types of instrumentation.

Figures 14, 15, 16:
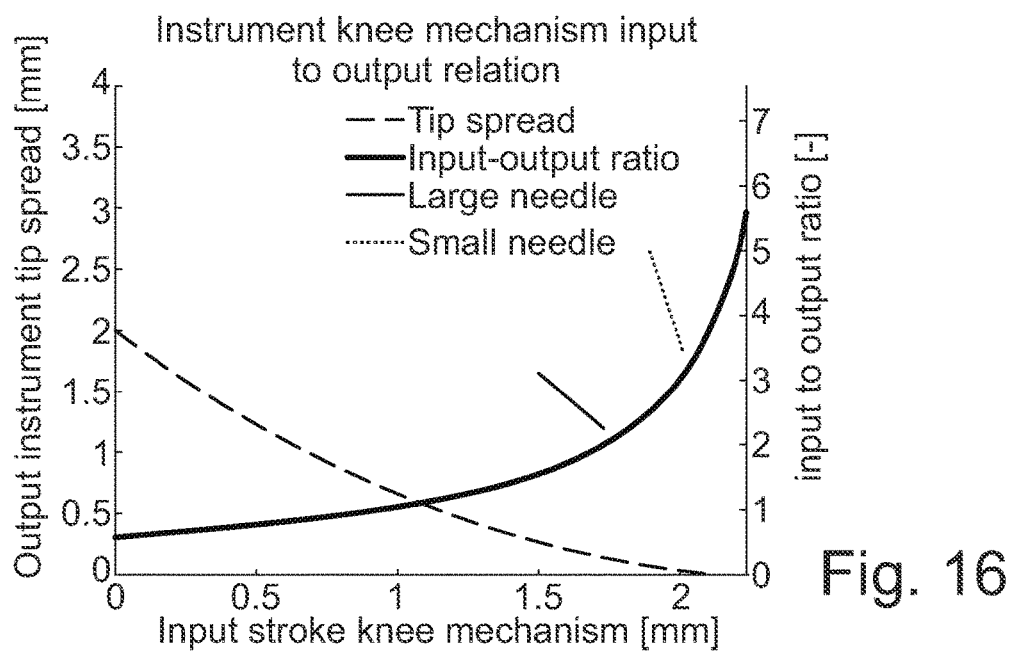
FIG. 14: an illustration of an embodiment of a custom needle holder, designed for robotic operation.
FIG. 15: an illustration of the instrument knee mechanism for symmetric actuation of the instrument.
FIG. 16: an illustration of the relation of input/output of the instrument knee mechanism.

FIG. 14 illustrates an embodiment of a custom instrument 106, designed for robotic operation.

The displayed instrument 106 is a needle holder 106, in particular for surgery, microsurgery or super microsurgery, in particular for anastomosis, although other types (e.g. forceps) are largely similar in layout and/or dimensions.

In this embodiment, the instrument 106 comprises two compact instrument beaks 142, an instrument hinge pin 144, two instrument handles 146 and two handle joints 148.

In an alternative embodiment, the instrument comprises more than one hinge pin 144 and/or more than two instrument handles 146 and/or more than two handle joints 148.

In this embodiment, an effective beak 142 length of 10 mm is selected for the custom needle holder 106. This dimension corresponds to the downscaling of the instrument 106 to approximately two thirds of a traditional needle holder 106 for a robotic arm 100.

This reduced beak 142 length serves to proportionally limit the maximum output arm for grasp. In turn, this again proportionally reduces the required amount of force applied at the handle 146 to clamp a needle 306 with a force of over 5 N at the beaks.

In general, the instrument beaks 142 each may have a length of less than 20 mm, in particular less than 15 mm.

Also in general, the instrument 106 may have a length of less than 50 mm, in particular less than 30 mm, in particular 20 mm.

Moreover, the selected dimensions allow for a one-to-one transfer of grasp from the handle-joints to the tip of the beaks.

In further contrast with the traditional type of needle holder, the custom variant features an inverted hinge mechanism. In other words, the instrument is configured and arranged for an inverted hinge mechanism.

Consequently, the beaks now close instead of open upon the spreading of the handles. This inversion serves the implementation of a knee mechanism for actuation of the instrument, as is described in the following paragraph.

FIG. 15 shows an illustration of the instrument knee mechanism for symmetric actuation of the instrument 106.

Shown is the instrument 106 according to FIG. 14.

On the left side, the instrument 106 is shown in the open state, wherein on the right side of FIG. 15, the instrument 106 is shown in the closed state.

Additionally, shown are two retainer guide pins 150, one knee link pair with two knee linkages 152, one stopper 154 and a knee mechanism central joint 156, which all are all comprised in the instrument retainer 138.

In particular, the operation of grasp is conveyed from the instrument actuation submodule 104 to the instrument 106 via a knee mechanism.

Following, the instrument retainer 138 is configured to actuate the instrument 106 by an inverted hinge mechanism.

In an alternative embodiment, the instrument retainer 138 could comprise more than one central joint 156, more than two retainer guide pins 150, more than one stopper 154 and/or more than one knee link pair 152.

The knee linkages 152 connect both instrument 106 halves to the central joint 156. Symmetric actuation of the instrument 106 hereby reduces to the controlled translation of this central joint 156 over the module centerline.

Further, a pushrod 158 is introduced (as part of the instrument actuation submodule 104), which acts over the centerline of the instrument actuation submodule 104.

The pushrod 158 comprises a spherical tip configured for contacting a matching socket in the knee mechanism central joint 156.

To this end, the instrument retainer 138 offers slots that serve as a straight-guide for the central joint's extended hinge pin 150. This guide together with the instrument hinge pin 144 itself fully constrains the instrument mechanism with respect to the instrument retainer 138, leaving only a single internal DOF for grasp.

Moreover, the second pin 150 on the central joint 156 serves to maintain the joint's 156 alignment with respect to the pushrod 158 to facilitate instrument 106 exchange.

The instrument knee mechanism is further illustrated in FIGS. 16-18.

FIG. 16 shows an illustration of the relation of input/output of the instrument knee mechanism.

Here, a 2.2 mm linear input stroke suffices to fully close the instrument 106 from its maximum spread of 2 mm at the tip.

FIG. 17 illustrates the dimensioning of the knee-mechanism.

In particular, a schematic representation of one instrument 106 half is provided, including one of the linkages from the knee-mechanism. The other instrument 106 half and knee may be considered their mirror image in the line A:A.

Moreover, the solid lines in FIG. 17 represent the instrument 106 in fully opened position. Conversely, the configuration for closed instrument beaks 142 is displayed in dashed lines. The stroke leading from one configuration to the other is in addition visualized using dashed curves.

The properties of the instrument 106 have already been described in detail in FIG. 14 and/or FIG. 15.

In surgery, it is not practical for the needle 306 to be grasped at the very tip of the instrument 106. Neither will it be operated near the instrument 106 base close to the instrument hinge pin 144.

It may therefore be assumed that for suturing the needle 306 will always be clamped somewhere in the 1 mm to 5 mm front section of the instrument beaks 142.

Hence, it now follows from the graph that the mechanism input to output ratio is always greater than 2.275 in the relevant section.

Therefore, an actuation force of 2.2 N at the knee mechanism central joint 156 would suffice to realize a grasp force of over 5 N for any needle 306 used.

Furthermore, over 30% of the input stroke is used to close the instrument 106 over the last 15% of its spread, where the needles 306 and tissue are grasped.

As discussed already for FIG. 14, the effective instrument beak 142 length $L_b$ is scaled down to e.g. two-thirds of a traditional microsurgical instrument 106.

Next, the length of the instrument handle 146 is selected equal to that at $L_b=L_h=10$ mm, in parallel consideration with the dimensioning of the knee mechanism and grasp drivetrain. Consequently, the required 2 mm maximum spread at the tip of the instrument 106 ($S_t=1$ mm) corresponds to an angular stroke of $\alpha_b=5.7°$ for each instrument 106 half.

The instrument handle 146 is now set at an effective angle $\beta_h=17.5°$ to the instrument beak 142, such that the spread at the knee ranges from 2 mm for the instrument 106 fully opened, to 3 mm for the beaks firmly closed.

Moreover, at $\beta_h=17.5°$, there is sufficient space for the knee mechanism central joint 156 to move in between the instrument handles 146, while $\alpha_k$ needs never be beneath a comfortable 42.5°. On the opposite end of the stroke, the knee angle is limited to a maximum value of $\alpha_k=85°$, as it is not desired for the knee linkages 152 to pass their unstable equilibrium position.

In addition, at least one mechanical end-stop/stopper 154 can be integrated into the instrument retainer 138 to block the knee linkages 152 before passing their critical angle.

In conclusion, for the dimensions listed above, a linear stroke $S_k$ of 2.2 mm now suffices as input for the knee-mechanism central joint 156 (to fully close the instrument beaks 142), cf. FIG. 16.

FIG. 18 shows an illustration of the instrument knee mechanism—preloading.

The illustration is based on the instrument(s) 106 properties disclosed in FIGS. 14 and 15.

As in FIG. 15, the instrument 106 is shown in its open position (left side), and in its closed position (right side).

The instrument 106 is shown here together with an instrument preload band 160 and a preload band guide pulley 162.

In general, the instrument preload band 160 and the preload band guide pulley 162 may be comprised in the instrument retainer 138.

Also, the instrument retainer 138 may comprise more than one preload band 160 and more than one preload band guide pulley 162.

Due to the nature of the contact between the pushrod 158 and the knee mechanism central joint 156, the pushrod 158 itself cannot exert a tensile force on the instrument 106. Hence, an additional restorative force is required to spread the instrument beaks 142 and maintain the contact between pushrod 158 and knee mechanism central joint 156.

To this end, the knee mechanism is preloaded by a preload band 160, in particular an elastic preload band 160, in particular a rubber band 160, applied to both the instrument handles 146 and the knee-mechanism central joint 156. This preload forces the instrument beaks 142 back into their open position, partly through the back-driving of the knee mechanism from the instrument handles 146.

However, in case the preload is applied only at the instrument handles 146, the resulting restorative force at the knee mechanism central joint 156 would strongly depend on the non-linearity of the knee.

Therefore, the preload band 160 is in addition looped around the preload band guide pulley 162, which is in particular located around a retainer guide pin 150, on the knee mechanism central joint 156.

In addition to maintaining the contact between pushrod 158 and knee mechanism central joint 156, the preload band 160 serves to remove play from the assembly.

As the preload band 160 is applied at the instrument handles 146 and tensions them together, the preload force will always act through the links of the knee mechanism. Consequently, the joints of the knees are always in contact in the direction corresponding to a closing action, such that no play is traversed upon the clamping of an object.

FIG. 19 shows an illustration of the instrument retainer holding the instrument.

The illustration is based on the embodiments disclosed in FIGS. 13, 14, 15 and 18.

The instrument 106 attaches to the instrument retainer 138 via the instrument hinge pin 144, which is situated directly at the base of the instrument beaks 142.

In particular, the inside of the instrument retainer 138 is shaped to accept a specific type of instrument 106.

In particular, the inside of the instrument retainer 138 comprises a specific instrument guide 163 to accept the instrument 106.

In contrast, the instrument retainers 138 contours and dimensions are identical across the range of compatible instrumentation. This serves to provide a universal interface at the instrument retainer 138 that matches its counterpart on the instrument actuation submodule 104 and retainer shell 140.

In addition, mechanical end stoppers 154 are integrated into the instrument retainer 138 that block the knees before passing their critical angle.

The instrument hinge pin 144 is convenient for attaching the instrument 106 to the instrument retainer 138, as it is the only part of the instrument 106 that does not move upon actuation of grasp.

Moreover, the instrument guide 163 of the instrument retainer 138 and hinge pin 144 together serve to constrain the position of each instrument half with respect to the instrument retainer 128 as well as each other.

The instrument retainer 138 is in turn supported on two plain bearings in the retainer shell 140 of the instrument submodule 126 (cf. FIG. 13).

To this end, the instrument 106 features a spherical surface at the instrument hinge pin 144, such that it remains within bounds of the forward bearing upon operation of grasp. These plain bearings serve to reduce friction compactly, without complicating the process of cleaning and sterilization. As the retainer shell 140 attaches rigidly to the instrument actuation submodule 104, it thereby positions and interfaces the instrument 106 and instrument retainer 138 with their respective drives.

For grasp, this interface amounts to establishing the preloaded contact between the pushrod 158 and knee mechanism central joint 156. For roll, on the other hand, the instrument retainer 138 integrates an inner gear that meshes with its counterpart on the instrument actuation submodule 104. Moreover, the resulting thickened end-section helps to preserve the circular shape of the torsion stiff retainer cone.

The instrument 106 in the instrument retainer 138 can be cleaned and sterilized disassembled from the instrument actuation submodule 104. This serves to improve the exposure of the instrument submodule's 126 inner surfaces. Moreover, the disassembled instrument retainer 138 with instrument mechanism is designed to feature only pin-joints and compact mating surfaces. These are similar in construction to the hinge area in a traditional microsurgical needle holder. Consequently, for the custom instrument 106, these contacts are assumed equally well suited to autoclave sterilization.

Furthermore, the instrument 106 and outer surface of the retainer (retainer shell) 140 may be brushed to remove organic contaminants such as blood prior to sterilization. The inside of the instrument retainer 138 in contrast is less prone to severe contamination and may be soaked and rinsed with cleaning agents. To facilitate this process, an anti-microbial coating can be applied to the instrument 106, knee mechanism, and retainer 138.

Moreover, this coating doubles in function to reduce friction in the mechanism joints and their contacts with the instrument retainer 138. The instrument beaks 142 in contrast must remain free from such coating, e.g. to prevent the needle from slipping.

Figure 20:
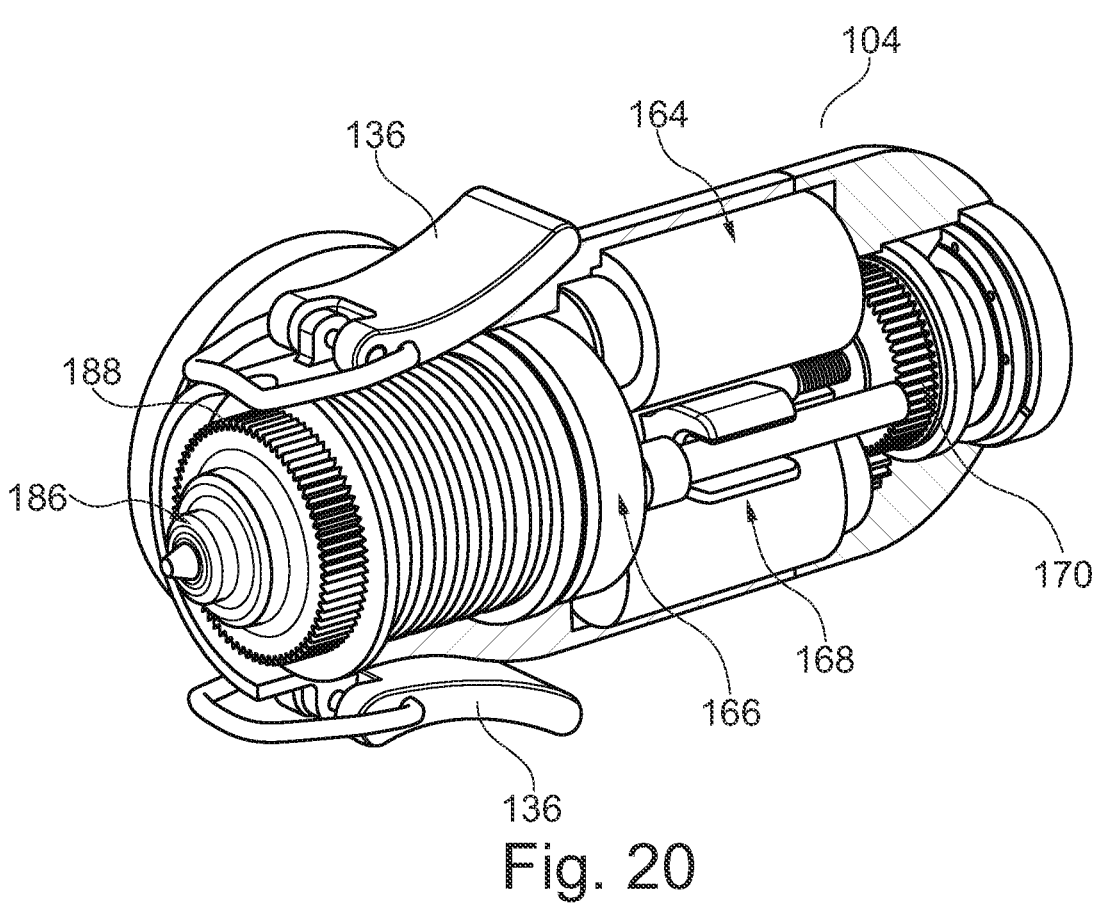
FIG. 20: an illustration of the instrument actuation submodule according to the disclosure.

FIG. 20 shows an illustration of the instrument actuation submodule 104.

As described previously, the instrument actuation submodule 104 comprises a first motor 164 and a first drivetrain 166 for actuation of the instrument roll orientation.

Further, the instrument actuation submodule 104 comprises a second motor 168 and a second drivetrain 170 for actuation of the instrument grasp orientation.

Further, the instrument actuation submodule 104 comprises a grasp instrument interface, a roll instrument interface, a compliant seal 186, a front frame instrument module, a rear frame instrument module and a frame cap.

As also described previously, the instrument actuation submodule 104 is configured to operate grasp and roll orientation of an instrument 106. In other words, the instrument actuation submodule 104 contains the actuators 164, 168 and drivetrains 166, 170 that allow full control over grasp and roll, when paired with the previously discussed instrument submodule 126.

Furthermore, the instrument actuation submodule's 104 enclosure provides an interface to the manipulator arm 250 that doubles as the pitch axis 130, as was already indicated in FIG. 12.

Figure 21:
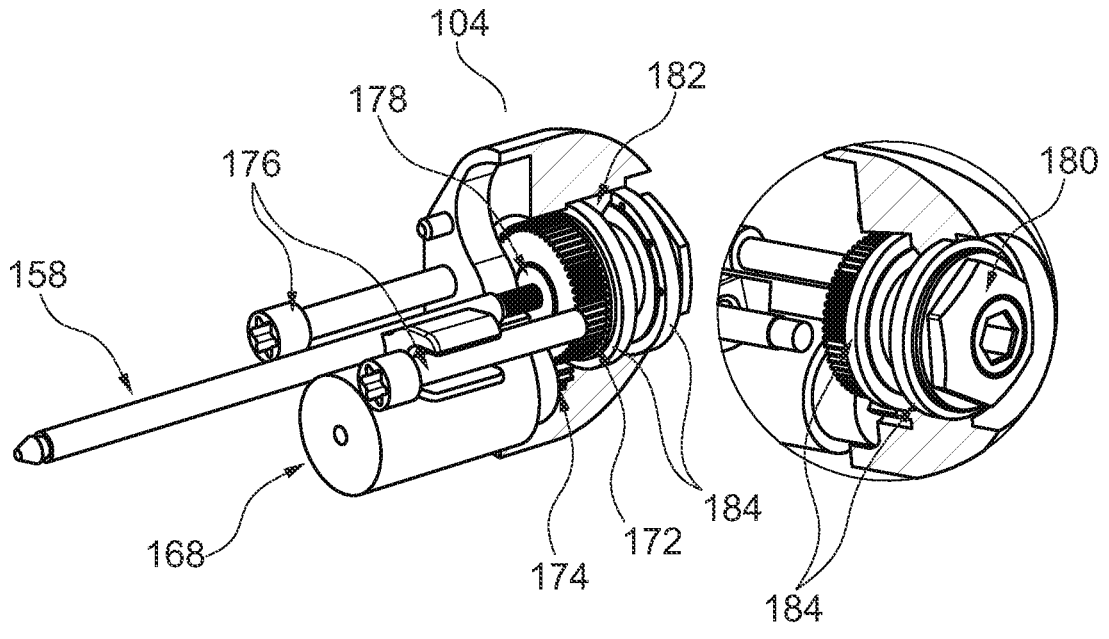
FIG. 21: an illustration of the instrument grasp module drive.

FIG. 21 shows an illustration of the instrument module grasp drive.

Illustrated is inter alia the grasp drive motor 168.

In this embodiment, the grasp drive motor 168 is a Stepper motor.

Further, there is a drive gear 172 and a motor pinion 174.

Shown is also the pushrod 158, a pushrod guide 176, as well as a leadscrew nut 178 and a preload nut 180.

Further, there is a bearing spacer 182

The actuation of instrument grasp can be described as follows (reference is made to FIGS. 15, 18).

As discussed for FIG. 15, the pushrod 150 positions the central joint of the knee mechanism 156 over a stroke of 2.2 mm along the instrument submodule 126 centerline.

The tip of the pushrod 158 is spherical and contacts a matching socket in the knee mechanism central joint 156.

This contact is maintained only by the instrument preload force, such that no additional coupling is required that could otherwise hinder instrument exchange.

The knee-mechanism central joint 156 rotates along with the instrument 106 upon actuation of roll. In contrast, the angular position of the mating pushrod 158 is constrained with respect to this axis. Hence, in the absence of rotation, a compliant seal may be applied to the pushrod 156 that serves as a flexible sterile barrier over the 2.2 mm linear stroke.

First, focus is shifted to the linear actuation of the pushrod 158. It is estimated that a force of 3.2 N would suffice, considering the knee-mechanism input-output relation and an estimate of an additional 1 N associated to friction and preload force.

Furthermore, the pushrod 158 is desired non-backdrivable, so no actuator effort is required for grasp once the instrument 106 is clamped. This measure serves to reduce heat generation in the instrument module 102, such that the effects associated to temperature variations may be minimal.

In addition, the pushrod 158 is configured to traverse its full stroke within one second to fully open or close the instrument 106.

Based on the consideration above, a M1.2 leadscrew with 0.25 mm pitch is selected for use in combination with a miniature Stepper motor 168. The combination of leadscrew and motor 168 is commercially available from the supplier in direct drive.

For actuation of grasp however, an additional spur gear transmission is included in the drivetrain 166.

A M1.2×0.25 mm stainless steel leadscrew serves to convert the rotation at the motor 168 to the required 2.2 mm linear grasp stroke at the pushrod 150.

The M1.2×0.25 mm leadscrew is threaded directly on the rear-end-segment of the pushrod 158 to form a compact union. As the sterile barrier does not allow the pushrod 158 to rotate around its longitudinal axis, the leadscrew nut 178 is driven instead.

This configuration is illustrated in FIG. 21 where the leadscrew 178 nut is incorporated into the body of the driven spur gear 172.

In turn, this body is suspended on a pair of miniature bearings 184, preloaded using a Belleville washer. This washer is tensioned by tightening the adjacent nut, while the rotation of the body itself is temporarily constrained using a hex key.

For actuation of grasp and roll, both standard Stepper motors can be selected factory fitted with a twelve teeth module 0.12 motor pinion 174 (pinion is rated up to at least the stepper's boosted holding torque of 0.39 mN m). Therefore, this standard configuration provides a convenient starting point in the development of the miniature transmissions for both grasp and roll.

In case of the grasp transmission, the pitch-diameter of the driven spur gear 172 may be based on the center distance of 4 mm between the pushrod 158 and motor 168. This results in a module 0.12 gear with 55 teeth, which corresponds to a transmission ratio of approximately 4.58:1 when paired with the motor pinion 174.

The direct drive specs multiplied by this transmission ratio would result in an axial force of 3.2 N, available for speeds up to 2.6 mm s$^{-1}$. This speed is sufficient to fully open or close the instrument 106 within one second, while the thrust can generate over 5 N of grasp force at the tip for all relevant instrument (needle) gauges.

In comparison to the M1.2×0.25 mm leadscrew, other variants have been considered as well. For example, a M2 leadscrew is commercially available with a smaller 0.20 mm pitch that allows twice the axial load and would increase grasp resolution. However, due to its larger diameter and reduced pitch, this variant offers only half the efficiency when compared to the M1.2×0.25 mm screw. Hence, as the stepper's torque is the limiting factor in the design, this reduction in efficiency would significantly reduce the available thrust at the pushrod 158. Overall, the 0.25 mm pitch leadscrew is found most suitably balanced when considering its diameter, efficiency, and rated linear force.

In the instrument module 102, the stepper motors 168, 164 and leadscrew are integrated side-by-side for compactness. Consequently, the driven spur gear 172 is selected based on their center distance, and to match the factory fitted motor-pinion. This may result in a transmission ratio of 4.58 for a certain gear combination. A first conservative indication of performance indicates a force of 3.2 N to be produced at the pushrod 158. This is based on the rated specs of the direct drive configuration of motor and leadscrew.

For validation, the following equation is now used to determine the required torque T to generate a linear force Ft based on the screw's lead L and efficiency e.

$$T = \frac{FtL}{2\pi e}$$

This computation shows that, neglecting other losses, a comfortable 0.1 mNm motor torque suffices for actuation of grasp. Taking into account the spur gear transmission, this torque serves to produce the maximal required push force of 3.2 N at the knee mechanism central joint 156.

Moreover, screws with an efficiency e<35% can be self-locking.

This results in a non-backdrivable grasp drive for the robotic arm 100 upon integration of the M1.2×0.25 mm leadscrew. This self-locking property allows the continuous load associated to the clamping of the needle 306 to be born by friction in the screw instead of a holding torque at the actuator.

The Support Miniature Bearings

The leadscrew nut 178 is suspended on a pair of commercial miniature bearings 184.

In one embodiment, these bearings have an inner diameter of 5 mm, an outer diameter of 8.2 mm, and width of 0.9 mm. They are available with a stainless steel retainer and ceramic balls, that are inserted between a split inner ring.

Instrument Handle Compliance

The instrument handles 146 of custom microsurgical instruments 106 feature a certain compliance that allows them to ex slightly upon the clamping of an object. This flexing offers a more gradual build-up of grasp force at the instrument beaks 142, and in addition serves as a preload and buffer towards the drive. Hence, minor variations in the position of the pushrod 158 can be accepted elastically without loosing grip on the instrument 106. Therefore, these variations do not require active compensation from the stepper motor 168, which would otherwise need to provide a constant correcting torque on the non-backdrivable leadscrew. Moreover, for other custom instrument 106 types such as the forceps, a high handle compliance can serve to limit the attainable grasp force while offering more control over its application.

In the following, it shall be focused on instrument 106 roll.

Instrument 106 roll is actuated from the final joint in the manipulator wrist, such that it may be controlled directly and independently at all times. Moreover, this axis requires a maximum angular velocity of π=2 rad s⁻¹ over its revolute stroke of ≥540 degrees. The design effort for the associated transmission will focus on conveying instrument roll through the sterile barrier over large rotations.

Figure 22:
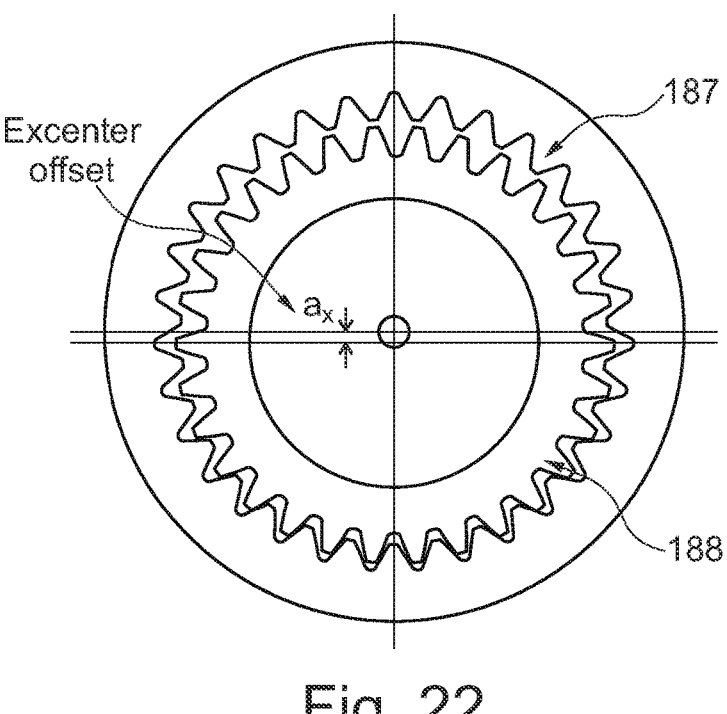
FIG. 22: an illustration of the hypocyclic drive transmission.

FIG. 22 shows an illustration of the hypocyclic drive transmission.

A variant of the hypocyclic transmission mechanism is proposed. Here, a driven internal gear 187 is integrated into the instrument retainer 138 (cf. also FIG. 19), and hence in extension it is directly linked to the orientation of the instrument 106. Moreover, this driven gear meshes with its external (roll external gear 188) counterpart on the instrument actuation submodule 104 (cf. FIG. 23), which in turn prescribed the instrument roll orientation.

The internal gear 187 is concentric with the roll axis and has 74 teeth module 0.12. In contrast, the external gear 188 has three teeth less, and therefore requires an offset ax of 0.21 mm from the roll axis to properly mesh.

Operation of the hypocyclic drive transmission in the essence boils down to rolling the external gear 188 along the inner contours of the internal gear 187. During this rolling motion, the center of the external gear 188 describes a circle around the hearth of the stationary internal gear 187. Furthermore, over one such revolution, the relative orientation between the internal gear 187 and external gear 188 shifts by the difference in their respective number of teeth. For the non-backdrivable gear combination described above, this amounts to a transmission ratio of 1/24.7.

In case of the instrument module 102 however, it is desired that the internal gear 187 rotates while the external gear 188 does not. This is realized by constraining the rotation of the external gear 188 while still translating its center over the offset circle introduced above. In this configuration, the hypocyclic drive remains driven from the external 188 gear, but the rolling motion now occurs at the internal gear 187 concentric with the roll axis 134.

Consequently, the sterile barrier is no longer required to seal a large rotation, but instead it now suffices to seal small in-plane translations. Consequently, a compliant seal 186 at the external gear 188 is able to convey an infinite angular stroke for roll.

In addition, a pair of relatively large open drive gears with only a small offset, allows sufficient space for integration of the pushrod 158 for grasp to pass through along the instrument module 104 centerline.

Figure 23:
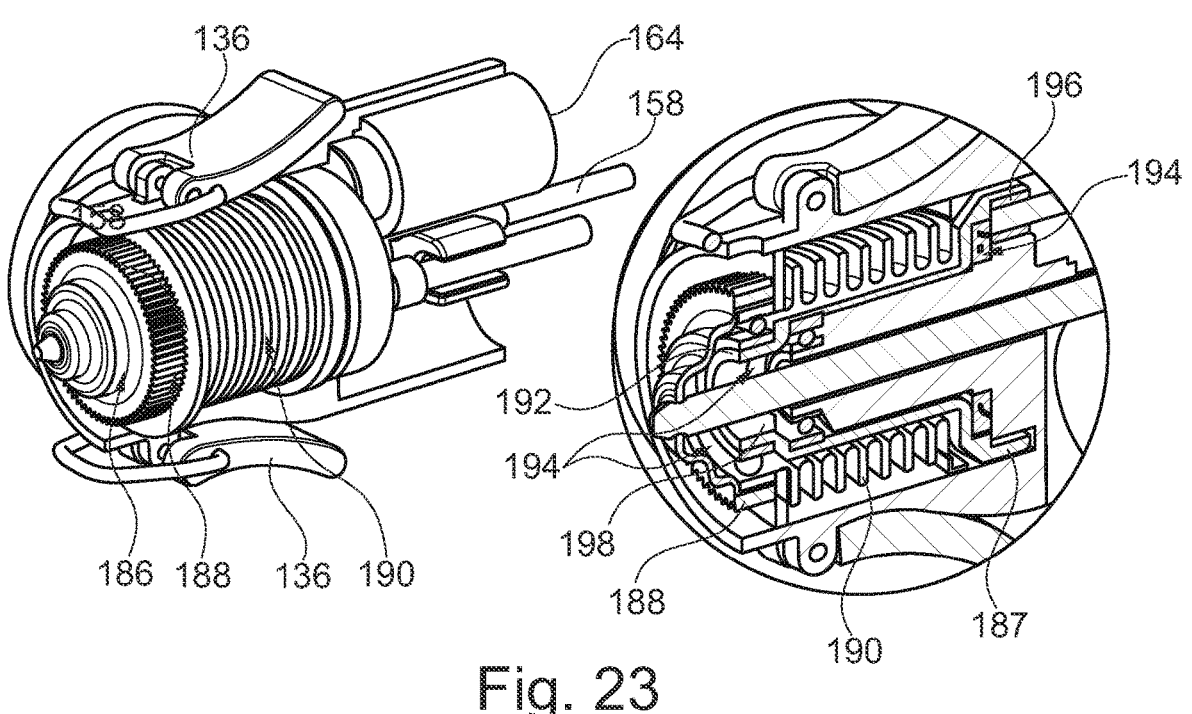
FIG. 23: an illustration of the role drivetrain.

FIG. 23 shows an illustration of the roll drivetrain.

In particular, on the left side of FIG. 23, the roll drivetrain is illustrated from the outside, whereas on the right side of FIG. 23, a cross section of the roll drivetrain is illustrated.

Although the hypocyclic drive introduced above is a key feature of the roll drivetrain, it requires auxiliary transmission components to make it functional. In the essence, the rotary motion at the stepper motor 164 needs be converted to a translation of the external gear 188 over the offset circle.

In addition, the external gear 188 must be coupled torsion stiff to the instrument module 102 enclosure, while remaining sufficiently laterally compliant to allow the in-plane wobble.

Shown is the compliant seal 186, the roll external gear 188, the bellow 190, the excenter shaft 192, roll drive ball bearings 184, the motor 164, the balance mass 198, the pushrod 158 and the motor pinion 196, which are explained below.

The Bellow Coupling

A miniature metal bellow 190 is integrated into the design that acts as the torsion stiff laterally compliant coupling to the external hypocyclic gear.

The bellow 190 must offer a compact torsion stiff coupling with sufficient lateral compliance to allow the excursion imposed by the excenter drive. Due to the scale of implementation and exposure to autoclave sterilization, an electroformed metal bellow variant may be most suitable. These can be produced leak tight with wall thicknesses down to 5 μm, which allows for high exibility and force sensitivity.

Here, the module housing is made to enclose the bellow 190 as well, in order to protect it from damage upon handling.

Design Requirements

Figure 39:
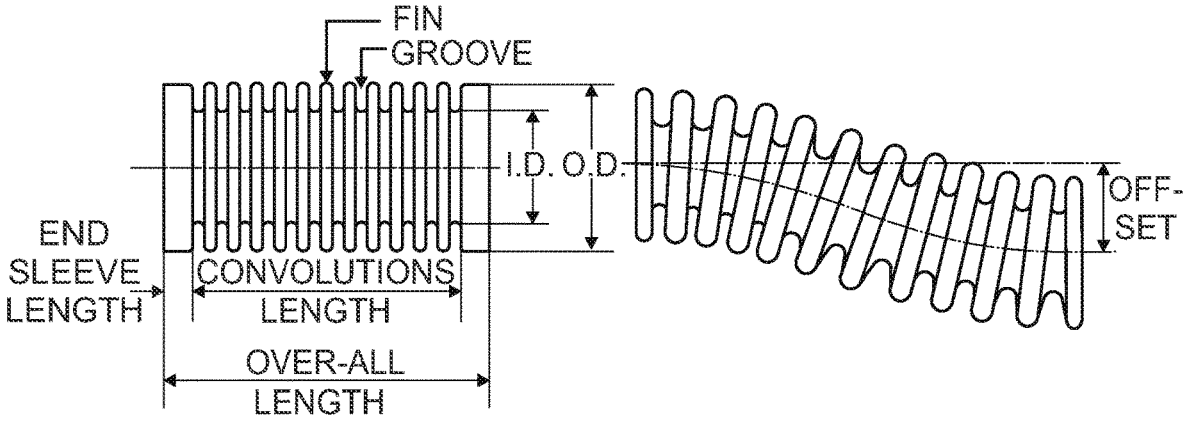
FIG. 39: a schematic illustration of a standard bellow with the relevant design parameters indicated.

In operation, an effective roll torque of 1.5 mNm at the instrument tip suffices. Nevertheless, for robustness, the bellow 190 must withstand a minimum torque of 15 mNm, which corresponds to the application of a 5 N maximum force at the instrument tip. Furthermore, the bellow 190 is desired to offer an infinite rotary lifetime for a parallel offset of 0.21 mm between opposite ends. This offset corresponds to that of the roll drive excenter and is selected in parallel with the dimensioning of the hypocyclic transmission. FIG. 39 provides a schematic illustration of a standard bellow with the relevant design parameters indicated.

The Excenter

Furthermore, the in-plane wobble is generated by an excentre shaft 192 that passes through the bellow 190.

On the drive side, the excenter shaft 192 features a 78 teeth internal gear that meshes directly with the standard motor pinion 186 on the motor 164 used.

Consequently, the transmission ratio from motor 164 to excenter shaft 192 is 6.5, which similarly to that of the grasp drive follows from their respective 4 mm center-distance.

On the opposite end of the excenter shaft 192, it features an excenter with 0.21 mm offset that drives the external (hypocyclic) gear 188.

The excentre shaft 192 assembly is laterally loaded by the bellow 190, which produces a 1.4 N reaction force to the imposed excentre offset.

To minimize the friction in the roll drive associated to this load, (ceramic) ball bearings 194 are selected that support both the excentre shaft 182 and hypocyclic gear.

These bearings 194 are loaded predominantly radially, and some play is accepted in their application. This allows the hypocyclic gear to align itself to its meshing counterpart, while temperature variations can freely be accepted along the excenter shaft 192.

Balancing the Roll Drive

To operate instrument roll at its maximum angular velocity of $\pi/2$ rad s$^{-1}$, the excenter shaft 192 must rotate at close to 6.2 revolutions per second. However, none of the centers of mass for the external gear 188, bearing 190, and excenter shaft 192 will naturally be incident with the axis of rotation. Hence, operation of roll continuously shifts these masses around, which introduces vibrations in the system. Therefore, an additional balance mass 198 in integrated in the excenter shaft 192 that serves to balance out the drive to reduce vibrations in the system.

The Compliant Seal 186

The contact between the knee-mechanism central joint 156 and pushrod 158 is maintained by a preload force. This allows the knee-mechanism to rotate freely with instrument roll, while the pushrod 158 remains stationary.

In the absence of rotation, a compliant seal 186 is applied to the pushrod 158 that exes to cover the 2.2 mm translation stroke.

As no relative motion is required between the compliant seal 186 and the pushrod 158, they may be rigidly bonded to provide a robust barrier against the passing of any contaminants.

The other end of the compliant seal 186 is attached to the external (wobble) gear 188 of the roll transmission, where it is bonded similarly. Here, the compliant seal 186 must comply to the 0:21 mm in plane offset associated to the wobble drive excenter.

The compliant seal 186 can be produced from an elastomer, such that it is suitable for repeated autoclave sterilization. As opposed to the band in the preload mechanism, the grasp seal is designed for low strain, such that the stresses introduced in the barrier are minimal. This serves to increase the life-span of the barrier and thereby reduces the costs and downtime associated to servicing.

Nevertheless, the compliant seal 186 must be inspected prior to surgery for safety, to verify it remains adequately bonded and shows no punctures. If all is in order, the risk of damage to the compliant seal 186 during surgery is regarded low and no more than that associated to the application of a drape 128, as is traditionally accepted.

Stepper Motor Control and Safety

Stepper motors allow for open-loop control, so no additional position sensors are required for operation of grasp and roll. The absence of such sensors contributes to the realization of a compact and robust design for the instrument actuation submodule 104.

Moreover, an eight core electrical connection for both actuators combined suffices in this case. Currently, this connection is maintained over the pitch stroke through sliding contacts. Alternative solutions without relative motion between the contacts can however be used and may still be considered to improve robustness.

Regarding safety, upon a fault in the stepper motor 164 drive system it can either stall or start jittering. Stalling may occur due to a loss of power, or a short circuit causing the motor 164 to exert a holding torque. For the latter, safety features can be included in the control circuit that limit the available power and shutdown the drive on overcurrent detection. The scenario of jitter may result in the case of wire break or a malfunction in the control sequence. It is argued that neither of these failure modes could result in uncontrolled and harmful motion at the end-effector, as both grasp and roll are individually actuated independent axes.

Furthermore, due to the specific commutation pattern required to operate the stepper motor 164, the fault scenario of runaway upon short circuit can be rejected. Single fault safety dictates that the fault conditions discussed above may not lead to an unsafe situation, neither directly nor due to an unawareness of the fault. Without position sensors on grasp and roll, the second condition must be satisfied. Here it is argued that the surgeon functions as an observer that may diagnose the loss of responsiveness for either of these axes. The surgeon controls the slave relative to the visual feedback provided through the microscope. Hence, he will act on the actual current state of the system with respect to the anastomosis, rather than attempt manipulations based on its supposed state.

Furthermore, it is argued that failure of roll does not lead to an unsafe situation, as there is no potential to do harm associated to this rotation. For grasp on the other hand, failure may occur with tissue or an object clamped stuck between the instrument beaks 142. In this scenario, the instrument submodule 126 may be loosened by the quick-lock clips 136, which simultaneously allows the instrument beaks 142 to spread. This proposed solution is considered equivalent to taking the instrument out of the actuation fingers upon fault.

No feedback is generated in the case of open-loop control and hence for grasp and roll no setpoint error is measured for the controller to act upon. Consequently, regarding safety, faults occurring in the instrument actuation submodule 104 are not communicated back to the controller and hence are argued not to have the potential to influence the control signal.

A mismatch between the controller input and actuator output occurs when the motor skips steps. Although this is generally undesired, it is not regarded unsafe behavior. Nevertheless, to prevent skipping steps, the available motor torque sits at a comfortable margin above that required for actuation of grasp and roll. Moreover, the required velocities and accelerations at the end-effector allow for a conservative motion profile. In addition, as neither the lead-screw nor the wobble drive is backdrivable, the actuators for both grasp and roll are relatively insensitive to disturbances at the end-effector.

Regarding performance, the surgeon precisely controls the instrument roll angle relative to its current orientation using visual feedback obtained through the microscope. It is argued that due to clutching, there is no intuitive absolute link to be lost between the input at the master gripper and the output at the slave instrument. Furthermore, the surgeon can achieve any roll angle independent from the instrument's installation orientation, as there are no bounds on its angular stroke and no other degree of freedom are affected.

The actuation of instrument grasp does similarly not affect any of the other degree of freedom, but it is however bounded to the opening and closing stroke of the instrument 106. Feedback on the motor current may be used for a homing procedure to define the bounds on a newly installed instrument. Homing is generally undesired, but this is accepted in case of grasp to deal with instrument variations. In addition, current sensing allows identification of the clamping point of the beaks around a needle, such that the motor may be shut down once the needle is firmly grasped. However, as lead-screw efficiency is relatively low, dedicated force sensing at the instrument may be considered to offer more detailed feedback. This could benefit the controller and surgeon.

The roll drivetrain must be able to offer a 0.5 N force at a maximum offset of 3 mm from the roll axis 134 (cf. FIG. 11), due to the curvature of the instrument beaks 142. This amounts to a minimal effective drive torque of 1.5 mNm.

In addition, the drivetrain is desired sufficiently robust to withstand a torque of up to 15 mNm, associated to a maximum force of 5 N applied at the instrument tip.

FIG. 24 shows an illustration of the pitch module 200.

In particular, on the left side, the pitch module 200 is shown without the pitch module enclosure 216, whereas on the right side, the pitch module 200 is shown coved with the pitch module enclosure 216.

Overall, the pitch module 200 comprises a pitch drive mechanism 202 (cf. FIG. 26), two flat cables 204, a motor plus absolute encoder 206, a plain bearing 208, a pair of pitch belts 210, a (forked) pull member 212, a bellow type compliant seal 214, a pitch module enclosure 216, an assembly guide bushing 218, a communication interface 220 and a yaw sensor magnet 222, Alternatively, the pitch module 200 comprises only a few of the mentioned elements.

The pitch module 200 is designed for a large angular stroke, such that surgeons may profit from the associated increase in instrument dexterity. To this end, a drive mechanism 202 is proposed that imposes the pitch orientation on the instrument actuation submodule 104 through a pair of flat metal pitch belts 210. The pitch drive mechanism 202 is integrated into the cylindrical enclosure of the pitch module 200/yaw shaft.

This pitch drive mechanism 202 serves to actuate instrument pitch over an angular stroke of up to 150 degrees.

The pitch belts 210 allow for a relatively compact pitch transmission, for which the short linear actuation stroke may be conveyed through a compliant sterile barrier.
Drive Stiffness First, the effect of the pitch transmission ratio $i_p$ is discussed, here, pulley radius $r_p$ is set to 7.5 mm and the effective arm length $r_t$ from the pitch axis to the tip of the instrument 106 is 31.6 mm. These values correspond to those of the proposed instrument module 104 design, for which the formula evaluates to a transmission ratio of approximately $i_p$=4.2.

$$i_p = \frac{rt}{rp}$$

The magnitude of a force applied at the instrument tip is multiplied by the above transmission ratio when acting at the smaller radius of the pulley. In addition, the resulting strain in the pitch drive system 202 is scaled up with the transmission ratio when experienced at the instrument tip.

These effects combined yield that the effective stiffness at the instrument tip is only a factor 1/17.75 of that offered at the pulley. This corresponds to a reduction in drive stiffness by the square of the transmission ratio.

The pitch module belt 210 is identified as the most critical member in its respective drivetrain.
Relevant Parameters in the Dimensioning of the Pitch Belt 210

The considerations result a 1.5 mm wide titanium belt with 4.25 μm thickness, wrapped over a pulley with 15 mm diameter.

A 2.5 N preload is applied to the pitch belt 210, which serves to increase the non-linear straightening stiffness and to remove play from the pitch drivetrain. Currently, the preload spring on the pitch belt 210 is applied in-line with the pull-member, but alternative solutions may still be considered to reduce its contribution to the overall drive compliance.

The effects of creep in the proposed pitch belt 210 can allow the angular position of the pulley to drift over time with respect to the pitch belt 210 when coupled only by friction. To prevent this discrepancy from forming, the pitch belt 210 is desired rigidly bonded to the pulley. This bond can be realized by small laser-welds, although these introduce stress-concentrations in the pitch belt 210 at the cost of a reduced load-rating and/or stroke.

Alternatively, adhesives may be considered that allow some stress relief over their contact area to reduce stress concentrations in the bond.

To this end, the pulley's theoretical maximum angular stroke of 180 degrees is reduced to 150 degrees, such that 3.9 mm of pitch belt 210 length is reserved for the bond.

Future development may produce a mechanical coupling between pulley and pitch belt 210 that can be disassembled more easily for servicing.

FIG. 25 shows an illustration of the forked pull member 212 and bellow type compliant seal 214.

The forked pull member 212 and the bellow type compliant seal 214 have already been illustrated in FIG. 24, but are here disclosed in more detail.

The parallel pitch belts 210 for pitch unite in a forked pull-member 212 on either end.

The cross-sectional area of the forked pull-member 212 is chosen significantly larger than that of the pitch belt 210 to compensate for their longer effective length.

Furthermore, the tensile forces in the pitch belt 210 are introduced in the forked pull member 212 to act along their center-plane, such that predominantly their in-plane stiffness is felt.

In plane bending moments at the base of the forked pull member 212 can however not be avoided, and hence the shoulders are designed wider to cubically increase their respective area moment of inertia. Consequently, the contribution of the pull-members 212 to the pitch drive compliance can be regarded insignificant in comparison to the parallel pitch belts 210.

The forked pull members 212 are screwed directly onto the pull-rods 224. This serves to adjust the drive preload and allows the forked pull-members 212 to be disassembled upon servicing of the compliant sterile barriers.

FIG. 26 shows an illustration of the pitch drive mechanism 202.

In this embodiment, the pitch drive mechanism 202 comprises at least one of a linear ball bearing 224, a non-locating ball bearing 226, a ball screw 228, a ball screw nut retainer 230, a sensor scale 232 (as part of the enclosure), a ball screw locknut 234, a preload spring 236, a stopper 238, a pull member 212, an absolute linear position sensor 242, a locating bearing support, 244, a torsion stiff coupling 246.

Alternatively, the pitch drive mechanism 202 could comprise not all of the mentioned elements.

Reference is also made to FIGS. 24 and 25.

The Pitch Drivetrain

With the forked pull-member 212 is place, actuation of pitch reduces to the controlled translation of the members along their centerline. To this end, each forked pull-member 212 is supported in a pair of miniature linear bearing 224, e.g. made of stainless steel with ceramic balls, suitable for exposure to the temperature cycle associated to repeated autoclave sterilization.

In operation, the upper and lower pull-member 212 move in opposite directions to maintain the pitch belt's 210 "straightening" preload over the pitch driven directly by a brushless DC motor.

A ball-screw 228 can be used featuring a section of both right-hand and left-hand thread. Similar to the linear ball bearings 224 in the pitch module 200, the ball-screw 228 and ball screw nut 234 can be manufactured in stainless steel.

Furthermore, standard options for the ball screw nut 234 include ceramic balls without lubrication, to make the configurations suitable for repeated exposure to autoclave temperatures. Such ball screw nut 234 is featured on either threaded section of the ball screw 228, moving symmetrically inward and outward between the pull-members 212.

A compact body encapsulates each ball screw nut 234 and clamps the pull-member 212 between two cylindrical contacts to constrain the rotation of the ball screw nut 234 around the ball screw 228.

In addition, stoppers 238 on the pull-members 212 constrain the axial position of the pull-member 212 with respect to the nut.

On one side, a preload spring 236 acts between stopper 238 and nut to preload the system to the selected tension of 2.5 N. Moreover, this preload spring 236 must correct the tolerances and thermal variations in the pitch drive for acceptable variations in the preload force. However, the preload spring 236 is also desired stiff, as it constitutes a serial link within the pitch drive mechanism. As stated above, alternative configurations to preload the pitch belt 210 may still be considered to improve the drive's overall stiffness.

The ball-screw 228 is located on one end in a matched pair of miniature precision ceramic angular contact ball bearings (in X-arrangement. In contrast, the opposite end is suspended floating in a ceramic deep-groove ball bearing. A standard bellow type torsion stiff coupling 246 is introduced between ball-screw 228 and motor such that any misalignment does not disproportionately stress the motor bearings.

For safety and performance the backdriving of pitch is argued to be non-essential, this could improve robustness of the drive during handling as it limits the maximum stress in the pitch belt 210.

The Pitch Drive Actuator

The pitch drive actuator/motor 206 is integrated within the confinement of the enclosing yaw shaft 116, cf. FIGS. 8, 24.

As there is significantly more space available here than in the instrument module 102, the motor 206 may be selected from the range pre-qualified for autoclave sterilization.

Such a motor 206 does not require any additional modifications and hence can be cost effective while simultaneously minimizing the chance of complications.

Position Sensor Redundancy

Per revolution, the absolute encoder integrated into the motor 206 offers 4096 steps of angular position feedback. This sensor can however not determine the pitch angle at startup without performing a homing procedure.

Therefore, this functionality must emanate from a second absolute position sensor, that serves double to provide the controller with measurement data redundancy. To this end, an absolute linear position sensor 242 (miniature linear induction sensor) is integrated with the (TPLA32) sensor scale 232 in a parallel configuration along the ball-screw 228.

This product offers a resolution down to 73 nm over an absolute stroke of up to 38.4 mm using the differential inductive sensing principle.

Although the absolute linear position sensor 242 is rated only for temperatures up to 100° C., the manufacturer has confirmed that both sensor 242 and scale 232 can withstand repeated exposure to autoclave temperatures when inactive.

Figure 27:
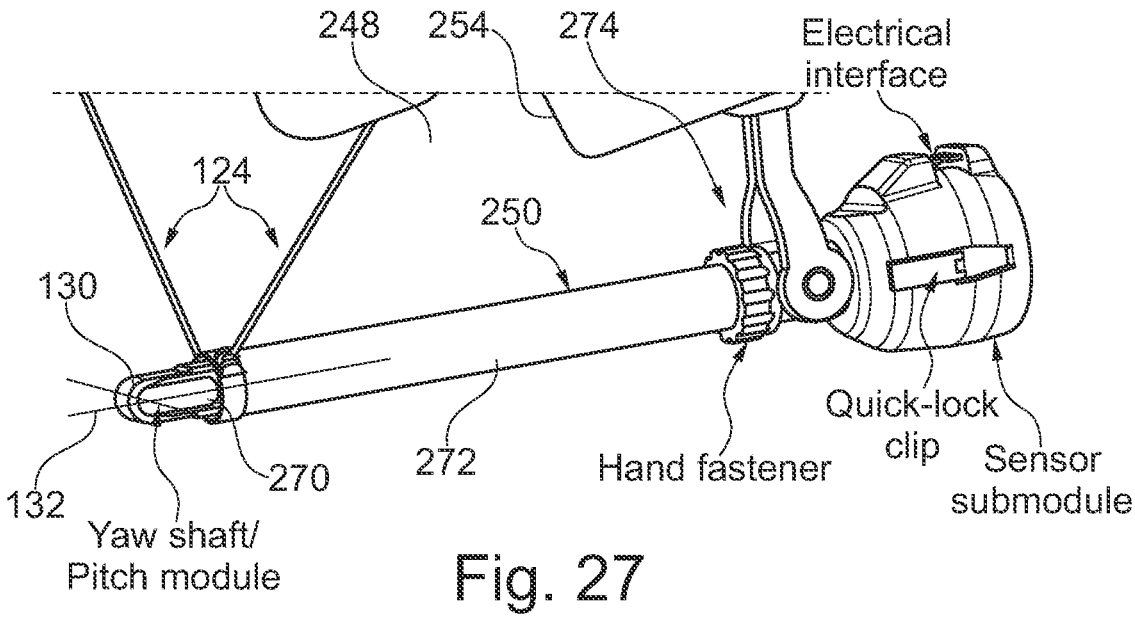
FIG. 27: an illustration of the yaw module.

FIG. 27 shows an illustration of the yaw module 248.

Concisely, the yaw module 248 consists of a pair of concentric tubes 270, 272 that together constitute the "manipulator arm" 250.

The inner tube 270 integrates the drive mechanism for pitch and provides an interface for the instrument module 102.

The outer tube 272, on the other hand, is suspended by the pair of struts 252 in the front and the crank module 254 in the rear, which serve to position the tube assembly in space.

Consequently, variations in instrument yaw result from the controlled relative rotation of the inner tube 270 with respect to the outer tube 272.

To this end, a direct drive motor is integrated in the outer tube that allows for an angular excursion of up to 150 degrees of instrument yaw, cf. FIG. 38.

Furthermore, the entire yaw module 248 is subject to autoclave sterilization and requires disassembly to improve exposure of the inner surfaces.

The Actuation of Yaw

A limited angle torque motor is selected for actuation of yaw. This torquer allows for an angular excursion of up to 150 degrees, providing a continuous torque of up to 70 mNm at a nominal voltage of 21V.

Moreover, due to the arrangement of windings in the stator, the motor requires no commutation in positioning the two-pole rotor over its entire stroke. Consequently, this aids in the development of a simple and robust drive, designed for consistent performance over a large number of disassembly, cleaning, and sterilization cycles. The selected limited angle torque motor is of the moving magnet type, where the rotor sits concentrically within the outer coil.

This product is supplied as a kit, containing only the magnet core and two-wire stator, without any housing or bearings. Off the shelf however, this kit is not yet suitable for autoclave sterilization. Therefore, an alternative magnet material was proposed for which the rotor can be produced to withstand autoclave temperatures. In contrast, the shielding of the stator against the elements is to be designed a feature of the yaw module 248 concept itself.

To this end, the volume associated to the 1.14 mm air gap between the torquer's rotor and stator is considered for the implementation of physical shielding. This gap provides sufficient space to cover the inner diameter of the stator with a thin impermeable shell that shields off the windings. Here, an adhesive serves to hold the shell in place and also lends it rigidity from the structure of the stator itself.

Moreover, this solution is inspired by the canned rotor type of motors, such as are frequently applied in fluid pumps.

The Measurement of Yaw

A pair of absolute encoders is implemented in the yaw module to measure the angular position of the limited angle torque rotor.

Similar to the pitch module, one sensor serves directly in the drive's control loop and is selected accordingly to offer high precision feedback.

The second sensor again operates in parallel to provide measurement redundancy, which improves system safety through fault detection. The performance of this redundant encoder is less critical and therefore allows more cost-effective and compact solutions to be considered.

Figure 28:
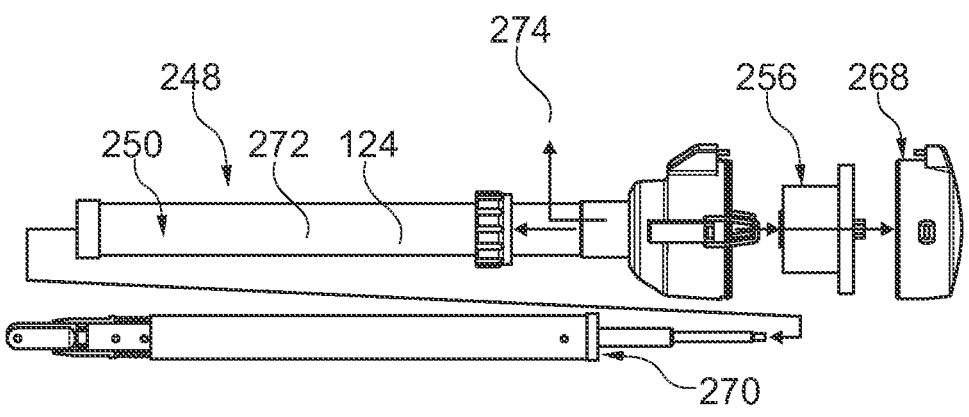
FIG. 28: a further illustration of the yaw module (disassembled)

FIG. 28 shows a further illustration of the yaw module 248 (disassembled).

In particular, the manipulator arm 250, the inner tube 270, the outer tube 272, the rotor submodule 256 and the sensor submodule 268 of the yaw module 248 are shown.

To facilitate the process of cleaning and sterilization, the yaw module 248 is designed to allow for easy (dis)assembly between consecutive procedures.

Most contaminants are assumed to result from patient contact and will therefore be concentrated near the instrument tip.

For this reason, the yaw shaft 270 is suspended floating on a plain bearing on the open end near the struts 252.

In addition, a pair of matched angular contact ball bearings in X-arrangement near the universal joint 274 serve to constrain the position of the yaw shaft 270.

These bearings are of the open ceramic type, where their exposed surfaces aid the process of cleaning and sterilization. Moreover, the length and upward angle of the manipulator arm 250 hinders contaminants traveling up the tube, such that the bearings experience practically no ingress.

Figure 29:
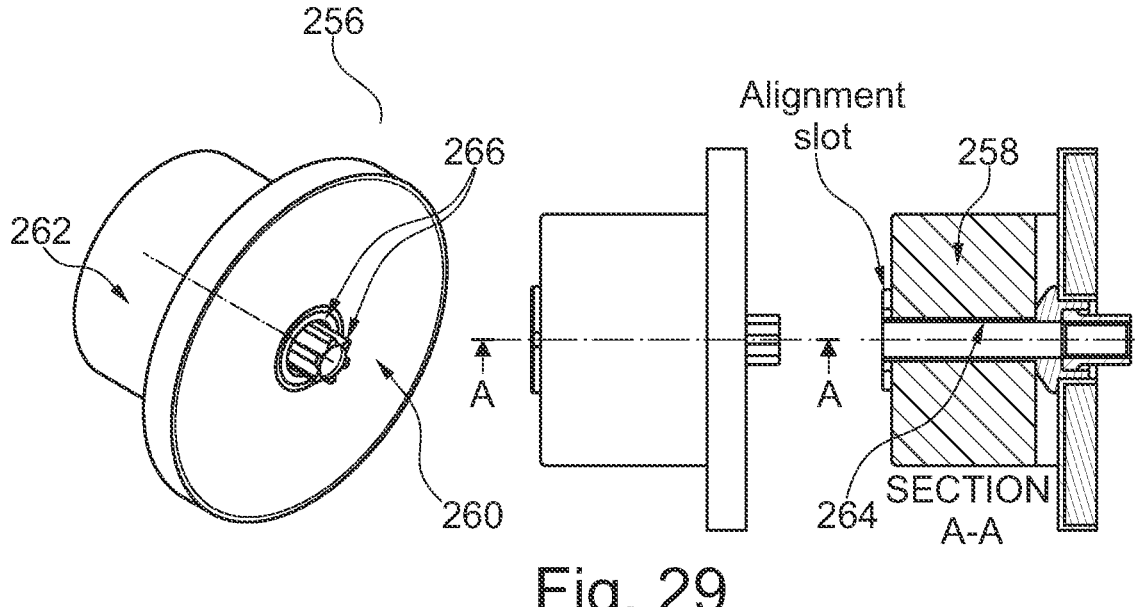
FIG. 29: an illustration of the yaw rotor submodule.

FIG. 29 shows an illustration of the yaw rotor submodule 256.

This assembly contains the rotor 258 of the limited angle torque motor, as well as that of the inductive encoder 260.

Both are passive components, concentrically bonded to a universal hollow shaft 264, where an adhesive serves to lock their relative orientation and seal the edges.

In addition, a thin protective shell 262 encloses the outside of the rotor 258. This protective shell 262 shields the rotor magnet 258 from corrosive agents and protects it against impact on handling. Moreover, the protective shell 262 provides smooth contours to the submodule that facilitates the process of cleaning and sterilization.

The yaw rotor submodule 256 can be mounted on the inner shaft/inner tube 270 of the yaw module 248 through the fastening of a single nut (anti-loss nut) 266.

Conversely, loosening this anti-loss nut 266 allows the rotor 258 to be removed from the outer tube 272, which simultaneously releases the yaw shaft 270 to be removed as well.

This disassembly step greatly increases exposure of the yaw module inner surfaces, and allows the manipulator arm 250 to be flushed through with cleaning agents.

To minimize the number of separate components upon disassembly, a retainer ring is glued in to the submodule that confines the anti-loss nut 266 nut to the rotor 258 in an anti-loss manner.

Upon assembly, a pin-in-slot construction prescribes the orientation of the rotor 258 relative to the yaw shaft 270. In addition, the tightening of the anti-loss nut 266 serves to preload the axial bond between components.

The resulting friction in this bond serves to eliminate the traversion of angular play during fine yaw manipulations.

Figure 30:
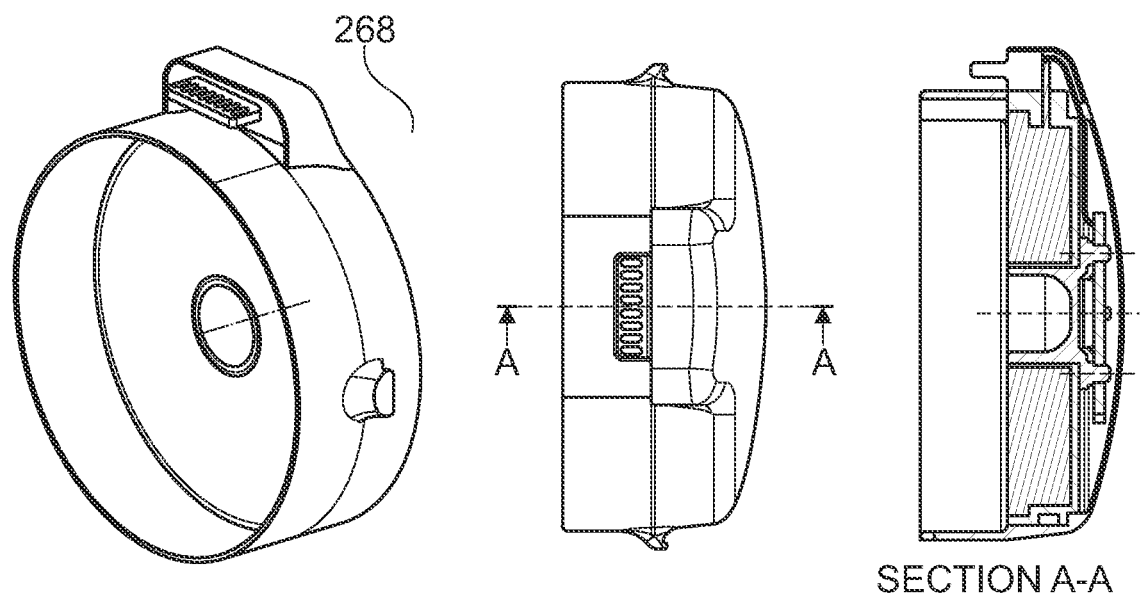
FIG. 30: an illustration of the yaw sensor submodule.

FIG. 30 shows an illustration of the yaw sensor submodule 268, providing a top- and section view.

This assembly integrates the active halves for the pair of absolute encoders that provide feedback on the angular position of the yaw axis. To this end, it provides a housing for the inductive encoder, while it shields the sensor chip in an enclosed volume.

A sterilizable connector is featured on top of the submodule that allows communication with the sensors.

Disassembly of the sensor submodule 268 from the system opens up the rear end of the manipulator arm 250, and thereby allows the rotor submodule 268 to be removed. To this end, the outer tube 272 contains a mounting rim that offers a precise fit with the inner diameter of the sensor housing.

Here, a pin and notch serve to prescribe the relative orientation of the sensors with respect to the manipulator arm 250. The axial position of the sensor submodule 268 is constrained by tensioning it against a ridge in the outer tube 272.

For convenient assembly, this tension is applied through the fastening of a quick-lock clip 136 on either side. An additional rubber ring on the mounting rim serves to seal the contact between the two components. This seal closes the sterile barrier and thereby prevents the spread of contaminants. Similar to the rotor, the sensor submodule 268 components may be sealed with adhesives to realize a compact and robust design without serviceable parts. Soft contours again assist in the efficiency of cleaning and sterilization.

Figure 31:
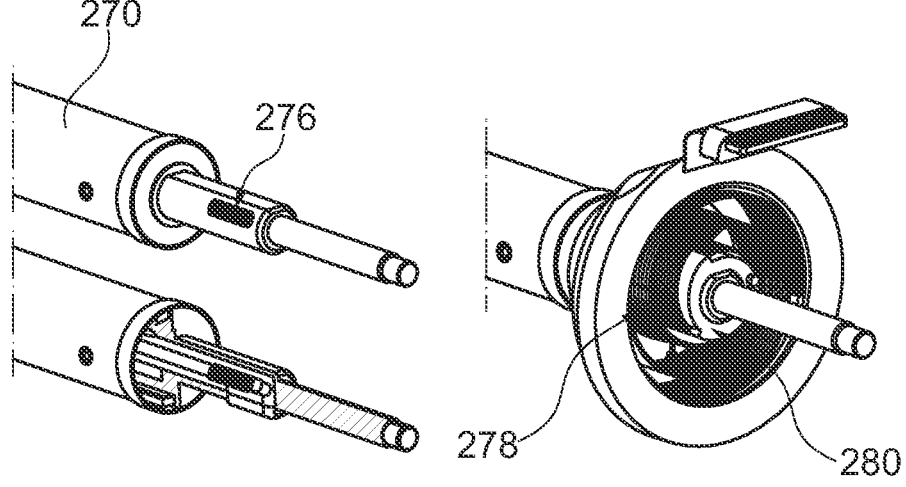
FIG. 31: an illustration of the yaw shaft radial electrical connection.

FIG. 31 shows an illustration of the yaw shaft 270 radial electrical connections.

The electrical connections for grasp, roll, and pitch are all routed through the yaw shaft 270 for compactness and robustness.

This yaw shaft 270 however also rotates over the 150 degree yaw stroke relative to the stationary manipulator arm 250. Consequently, the electrical connection between the two must be designed to function reliably regardless of this relative motion.

Moreover, as the connection passes through the sterile barrier of the manipulator arm 250, the design has to be sterilizable itself as well.

For safety and robustness, a semi-fixed plug type connection may be used over the use of sliding contacts that feature relative motion in operation.

Here, the yaw shaft 270 integrates multiple-contact radial connector segments 276, that face radially outward and are ground flush with the yaw shaft 270 itself.

To reduce the required length for the connector, three such radial connector segments 276 are spaced evenly over the circumference of the yaw shaft 270 in parallel.

The mating connector for the shaft-plug is displayed on the right of FIG. 31, and is directly suspended on the pair of angular contact bearings in the manipulator arm 250. Consequently, upon assembly of the yaw shaft 270, the plug automatically snaps in place and is secured there through the fastening of the rotor nut.

A at side on both the shaft and connector ensures that they can only be mated in the correct relative orientation.

Furthermore, the conductive patches in the connector 280 are placed on feathers between cuts that are sealed by a durable sterilizable rubber compound. This serves to make the patches slightly compliant in radial direction, which preloads the contacts while maintaining a smooth outer surface for robustness and to facilitate cleaning, and sterilization.

With the plug-type connection between the shaft and connector 280 defined, focus is now shifted to the relative rotation between the connector 280 and the outer tube 272 housing.

To this end, three sets of spiral flat cables 278 are designed to spiral outward from the central connector 280.

Similar to the contact patches on the shaft, these are implemented in a parallel configuration to safe space in the axial direction.

Each of these cables 278 consists of twelve 28AWG multi-stranded cores with a flexx-Sil jacket.

When the yaw shaft 270 turns clockwise, the connection is maintained as the spiral flat cables 278 reduce their local radius and tighten closer around the plug. Vice-versa, for a counterclockwise rotation, the spiral flat cables 278 expand again.

Furthermore, to prevent over-stressing the spiral flat cables 278, end-stops are implemented that contact a pin in the manipulator arm 250 that limits the rotation of the central connector 280 to the maximum stroke of 150 degrees.

The surfaces of the connector 280 and spiral flat cables 278 are relatively well exposed to steam sterilization in the autoclave. This may be further enhanced by moulding the cable base on either end in a compliant sterilizable rubber to fill the least exposed areas.

In addition, this helps smoothen the contours and serves as a strain-relief. The inner diameter of the spiral flat cable housing is designed to match that of the motor stator, such that they form one smooth continuous surface. For cleaning of the spiral flat cable assembly, it may again be flushed through with cleaning agents once the rotor 258 and yaw shaft 270 are removed.

Moreover, with the spiral flat cables 278 integrated behind the motor, they are relatively well shielded against accidental contact by an operator, which could otherwise damage the connection.

Figure 32:
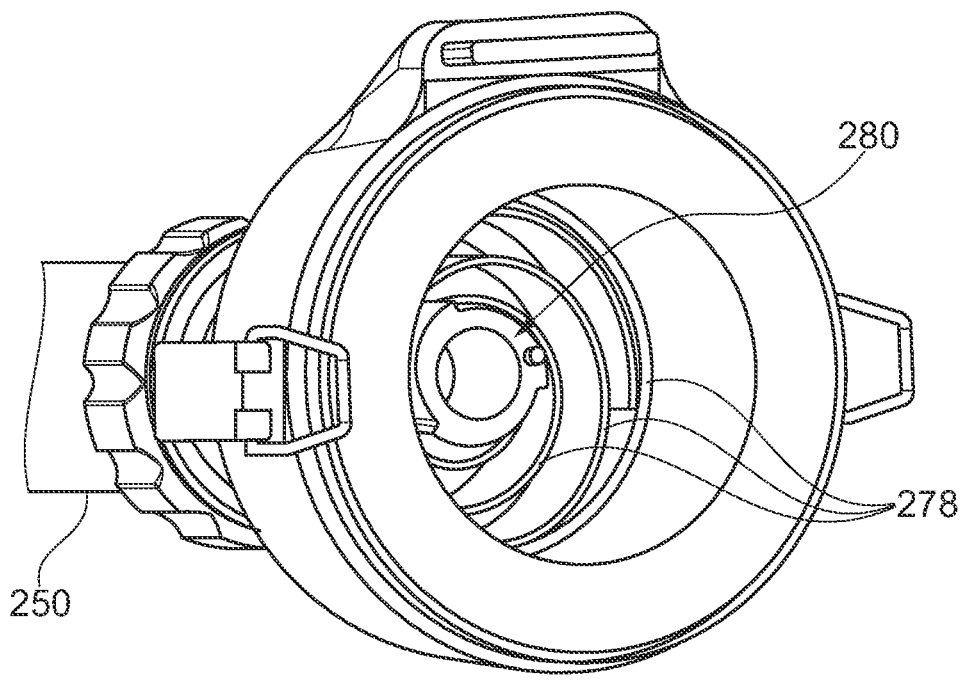
FIG. 32: an illustration of the disassembled yaw module.

The disassembled yaw module 248 viewed from the rear is displayed in FIG. 32.

FIG. 32 shows an illustration of the disassembled yaw module 248, viewed from the rear.

In particular, the central connector 280 and the spiral flat cables 278 are shown.

In FIG. 8, also the crank modules 122, 254 of the instrument position module 120 are shown.

The crank modules 122, 254 shall now be explained with regard to FIGS. 8 and 33-36.

The two struts 252 attached to the manipulator arm 250 are each actuated by a crank module 122 and together control the instrument position in two degrees of freedom.

Here, a rotary Lorentz motor serves to position the crank over an angular stroke of 60 degrees.

The drive is controlled using feedback from a redundant pair of absolute position sensors. A protective cover in turn encloses the actuator and encoders to shield them off and prevent interference with the drape 128.

The crank arm 286 protrudes from this cover to drive the strut 124, which is attached to it via a spherical joint 292.

A high level of symmetry in design allows identical modules to be used for the actuation of the struts 124 on either side of the base frame 284.

Moreover, the crank module 122 may be assembled and tested independently as a functional subsystem of the robotic arm 100.

The crank module 122 operates from inside the drape 128 during surgery, as previously indicated, such that it requires no sterilization afterwards. This serves to reduce the repeated effort associated to the cleaning and sterilization of the system in between procedures.

Moreover, the design constraints on the crank module 122 significantly relax when exposure to autoclave conditions is avoided.

The Crank Actuator:

A rotary voice coil actuator is integrated in the crank module 122 to offer direct drive actuation of the crank 286.

The rotary voice coil actuator is of the moving coil type, with a stationary set of magnets and yoke. Both the coil arm and yoke are customized to better suit their integration into the crank module 122.

While the yoke is made to accept the standard magnets, it provides additional pockets for the crank arm bearings 282 and a support structure for the position sensors. The crank arm 286 in turn directly integrates the standard motor coil 288 and is extended past its hinge to provide an interface for the strut 124 and encoder scale.

The concept design for the crank module 122 features an inline direct drive for high precision actuation of the strut 124 with minimal disturbances.

Moreover, this drive offers zero backlash while the rotary Lorentz motor allows cog free operation.

The crank 286 is supported on a pair of preloaded precision deep-groove ball bearings 282 that introduce only a small amount of friction. This friction however acts at a small radius and combined with a light and stiff design of the crank 286 this serves to minimize the effects of virtual backlash. Besides friction in the crank arm bearings 282, relative motion between contacting surfaces is limited to the ball joint 292 at the strut 124. Due to the small number of components and with minimal wear, the drive can be regarded relatively robust and low maintenance for consistent performance over its lifetime.

Furthermore, the motor 288 allows two-wire single phase operation, which serves to simplify control and the associated electronic circuits integrated in the system.

Position Feedback:

Precise control over the Lorentz motor requires feedback from a high resolution angular position sensor.

In case of the robotic arm 100, this feedback system is required to provide an absolute reading with a redundant measurement signal for safety.

To this end, rotary encoder modules can be considered for measuring directly at the crank rotation axis. However, without any additional form of transmission, such sensors are limited to $\frac{1}{6}$ of their measuring scale due to the 60 degree crank stroke.

Furthermore, actuation of the strut 124 at a crank arm 286 of 70 mm would already require a 19-bit encoder system to distinguish a 1 μm translation at the strut 124. Such rotary sensors do not match well with a compact design for the crank module, that is desired especially slender near the crank and hinge to facilitate draping.

Consequently, the use of a limited angle arc shaped encoder is proposed, which measures away from the axis of rotation at a larger radius for increased resolution. Moreover, the implementation of such an encoder system pairs well with the construction of a balancing mass for the crank arm. The proposed arc shaped encoder system is based on a commercial product.

Here, the readhead may be stationary, such that no disturbances are introduced due to flexing of the data cable. The absolute scale is featured on a 0.15 mm thick stainless steel strip, which allows a curvature along its length down to a minimum radius of 50 mm. The arc segment 298 on the crank is in turn designed to accommodate this scale at the minimum radius, and it provides a slot to aid in its alignment and fixation.

For measurement redundancy, an identical pair of these optical encoder systems are integrated side-by-side within the crank module 122. A more cost-effective solution could be implemented for the redundant sensor, as its performance is typically less critical. For the crank module 122 however, the symmetry and simplicity of two identical systems may be used for reasons of compactness and performance.

Although the arc segment 298 increases inertia of the crank 286, it serves to balance its mass and that of the strut with respect to the axis of rotation. In addition, due to the large measurement diameter, the maximum resolution at the strut joint with this position sensor is 1.4 nm, depending on the read-head protocol selected.

Figures 33, 34, 35:
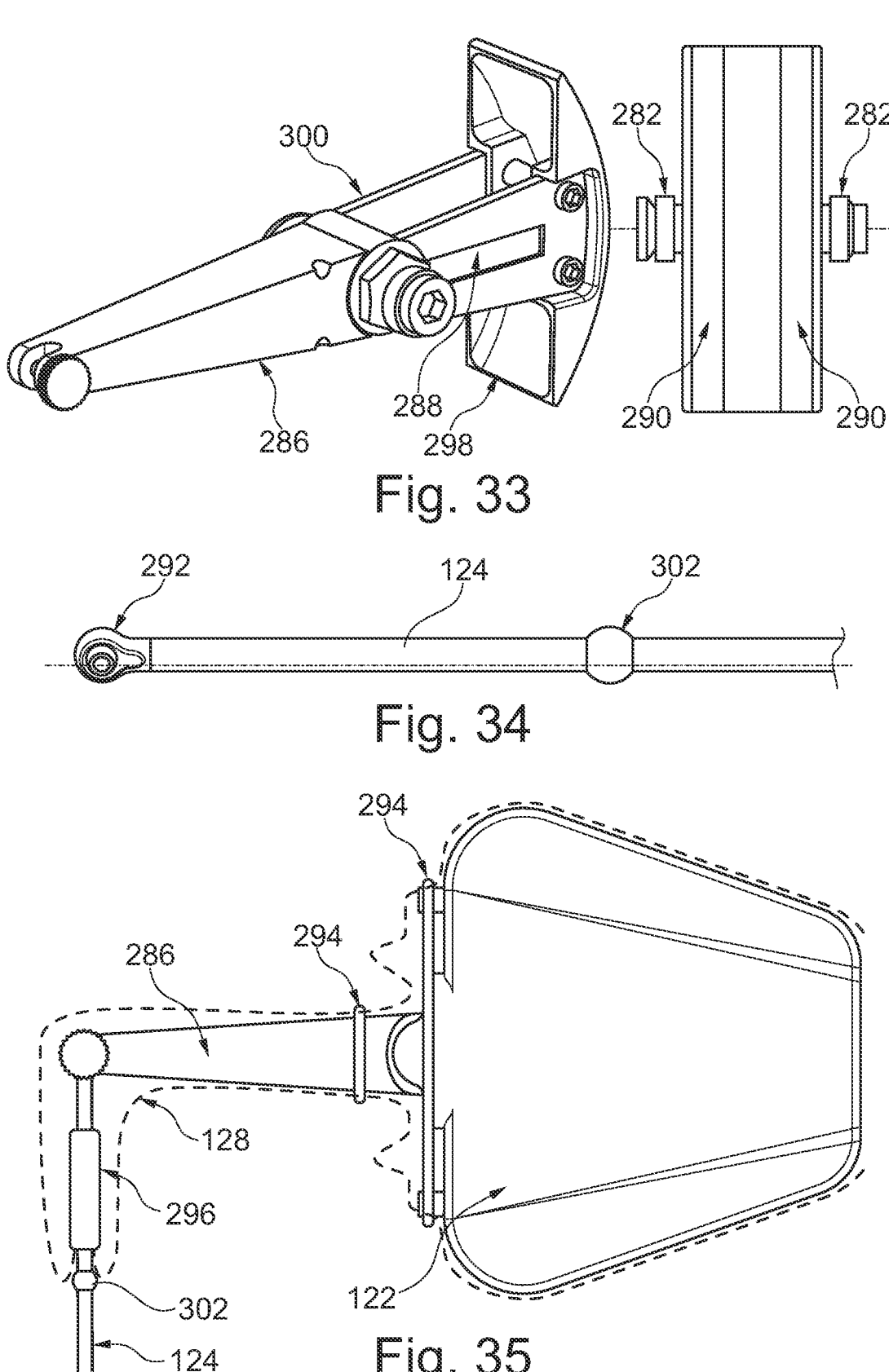
FIG. 33: an illustration of the concept design of the crank module.
FIG. 34: an illustration of the struts.
FIG. 35: an illustration of the draped crank module.

The Crank:

The concept design for the crank module 122 is displayed in FIG. 33. It directly integrates the rotor coil 288 from the Lorentz motor, which serves to position the crank arm 286 over its angular stroke of 30 degrees in either direction.

This coil is rigidly bonded to the crank arm 286 using an adhesive, such that the method of mounting is similar to that for a typical hard disk drive voice coil. The front end of the crank 286 features the interface for the strut 124, while the arc segment with double encoder scale 290 is placed to the rear. Accurate positioning of the strut 124 benefits from a stiff design for the crank 286, with low inertia.

The Crank Arm 286

The strut 124 attaches directly along the hearth line of the crank arm 286, such that the resulting torsional moment introduced in the crank is minimal under load. Furthermore, due to the manipulator geometry, the main component of the force acting through the strut will always be in plane with the Lorentz motor rotation.

Nevertheless, depending on the sideward sway of the strut 124, a smaller bending moment is also introduced in the horizontal plane of the crank 286.

Consequently, a closed box structure is employed for the crank arm 286 that offers high stiffness in both planes, while mass and inertia remain relatively low.

To this end, the inner material may be removed from the crank by machining its bottom surface away, and gluing in a matching cover afterwards. This cover serves to close the box and thereby lends it stiffness through the suppression of the internal degrees of freedom associated to an open box. Moreover, less material toward the tip of the crank 286 requires less mass for balancing towards the rear, and hence this serves double to reduce inertia.

Attachment of the Drape 128:

For the closed box design of the crank 286, as introduced above, the most profound effect on stiffness is gained through an increase in the effective height of its side-walls.

Nevertheless, the crank 286 is simultaneously slender at the hinge to minimize interaction with the drape 128 upon repositioning. In case the drape 128 is hindered in this regard, it introduces disturbances in the crank 286 and may even restrict its range of motion.

As discussed previously, the relative motion in the drape 128 between the operated crank 286 and stationary base frame 284 is desired minimal. Therefore, it is desired that a well-defined interface from crank 286 to drape 128 is provided, as well as one from drape 128 to base frame 284. Regarding the drape 128 as a sheet, it is most compliant when loaded in out-of-plane bending instead of an in-plane tensile force.

To this end, the drape 128 is proposed to be applied in a plane perpendicular to the crank 286 and fastened close to its hinge. There it can be cost-effectively held in place by bands 294, e.g. disposable sterile rubber bands, such as are well available commercially. This concept is illustrated in FIG. 35, in parallel to the sealing of the drape around the strut.

The Coil Support Structure 300 and Arc Segment 298 (Cf. FIG. 33):

To the rear of the hinge, the crank 286 is loaded in the plane of rotation by the Lorentz force at the rotor coil 288, and the inertial force of the arc-segment 298.

These loads are transferred through the slots of the Lorentz motor by the coil support structure 300. This structure consists of two parallel plates, which are situated inline with the side walls of the crank 286 to offer high in-plane stiffness. The coil support structure 300 is illustrated in FIG. 33.

Moreover, this coil support structure 300 and arc-segment 298 move between the magnets of the Lorentz motor. For electrical conductors such as aluminum, Eddy currents will be generated as the structure experiences a change in magnetic field upon rotation of the crank 286.

Therefore, the material for the coil support structure 300 is selected an electrical insulator, such that no prohibitive Eddy currents are generated.

The aluminum nitride machinable ceramic is selected for the coil support structure 300. It is an electric insulator with high thermal conductivity of 180 W=mK and low thermal expansion of 4 μm=mK.

In this capacity, the coil support structure 300 allows heat generated at the rotor coil 288 to be dissipated to the crank 286, which may in turn serve as a thermal buffer and simultaneously increases the surface area for heat loss.

The crank arm 286 and arc-segment 298 are both machined from aluminum to limit production costs. The aluminium nitride in contrast is more expensive, and hence it is integrated such that the support structure 300 can be cut out of thin sheet material. The difference in thermal expansion between aluminum and ceramic could introduce hysteresis in the crank 286.

Therefore, the crank 286 is assembled with its components permanently bonded using adhesives. Permanent bonding is allowed here as the resulting crank 286 may be integrated as a single submodule during the assembly of the Lorentz motor.

Direct Drive Considerations:

A consequence of a direct drive is that the required forces must be realized directly by the actuator, without further reduction associated to a transmission. Consequently, continuous holding forces result in a higher heat dissipation in the actuator. The Lorentz motor considered is a moving coil variant.

To improve heat dissipation to the frame, a moving magnet with stationary coil may be considered.

Alternatively, a thin thermal strap could be considered to offer a thermal path for cooling the coil to the frame. For future developments, the collection of data representing the force required during surgery may provide additional insight into heat generation at the actuator.

FIG. 34 shows an illustration of the struts 124.

The struts 124 constitute the links between the manipulator arm 250 and the pair of drive cranks 286 overhead (see also FIG. 8)

In this capacity, the struts 124 transfer the input motion at the crank module 122 directly to their interface at the tip of manipulator arm 250.

Correspondingly, each of the crank modules 122 can actively control the manipulator arm 250 by prescribing a single degree of freedom to its position in space. Moreover, this manipulation directly translates to control over the position of the spherical wrist, and hence in extension prescribes the position of the instrument 106 itself.

Moreover, each strut 124 may only link the crank 286 to the manipulator arm 250 in one degree of freedom to prevent overconstraining the system.

To this end, the strut 124 features a spherical joint 292 on either end, that allow the strut's 124 body to orient itself along the line of operation.

Hence, the struts 124 will predominantly experience axial loads, with only small bending moments resulting from friction in the joints.

To transfer this axial load, a slender stainless-steel tube efficiently serves as the body for the strut 124 to provide high stiffness for a lightweight design. In addition to stiffness, the tubes are dimensioned primarily for robustness. This serves to minimize the chance of damaging the struts during handling or transport in the autoclave trays.

Here, the edges are sealed and smoothed to prevent the ingress and buildup of contaminants. Moreover, the use of corrosion resistant materials combined with a simple and smooth design makes the strut suitable for repeated autoclave sterilization.

Consequently, the ability to operate the struts 124 outside the sterile barrier serves to significantly reduce visual obstruction by the drape 128, as previously described. Although the struts 124 need to be detached from their cranks 286 upon sterilization, they may remain attached to the manipulator arm 250 to reduce the effort of (dis)assembly.

Closing the Sterile Barrier Around the Strut 124:

As illustrated in FIG. 35, the crank modules 254 operate from within the sterile barrier during surgery.

Hence, the struts 124 must pass through this barrier to interact with the manipulator arm 250 on the outside. Consequently, it is important for safety that the sterile barrier is well sealed to the struts 124 such that no contaminant may pass through in operation.

To this end, the drape 128 is designed with a tapered extension at the end of the sleeve covering the crank 286. This tapered extension in turn ends in a perforated hole that allows the spherical joint 292 of the strut 124 to be fed through.

In addition, the strut 124 contains a spherical end-stop 302 (cf. FIG. 34) that cannot pass through the hole, thereby locking the drape 128 in position.

Closing the sterile barrier now amounts to fixating and scaling the drape 128 around the strut 124 using surgical tape 296.

Subsequently, the drape 128 can be inverted to fold back up away from the strut 124 to cover the crank 286 after the attachment to the spherical joint 292 has been secured, cf. FIG. 35.

The Spherical Joints 292:

The strut 124 uncouples from the crank 286 at the spherical joint 292 for disassembly upon sterilization.

Spherical joints 292 where the socket can snap-on to the ball-stud allow a simple coupling procedure and good access to the contact surfaces during sterilization. A consequence is that separation often requires increased tolerances, reduced stiffness, or a spring preload which could increases friction or play. Moreover, such spherical joints 292 may lead to high forces being exerted on the crank during (un)coupling by an operator.

Therefore, the spherical joint 292 itself is selected non-separable, so it may be produced to tight tolerances for smooth operation without a high preload.

A two-side open socket is selected to reduce the inaccessible surfaces, and an antibacterial sterilizable Teon coating may be applied to the socket to reduce friction.

The spherical joints 292 of the struts 124 are semi-permanently fixed to the manipulator arm 250 via metal pins, as they require no separation upon cleaning and sterilization.

On the side of the cranks 286 however, the struts 124 must be detached between procedures for installation of the drape 128 among others. Here, an anti-loss hand-screw serves to tension the spherical joint 292 against a spherical contact on the opposite face such that the spherical joint 292 is rigidly locked in position.

The Central Crank Module 254 for the Manipulator Arm 250:

An additional third crank module 254 serves to control the seventh and last degree of freedom at the instrument 106 by actuating the manipulator arm 250 directly in its center of mass.

This third crank module 254 can be referred to as central crank module 254.

Moreover, this central crank module 254 also passively constrains the manipulator arm 250 in three degrees of freedom, such that it is now fully constrained.

Consequently, the design of this third (central) crank module 254/crank arm 286 is different from the crank modules 122 interacting with the struts 124.

Figure 36:
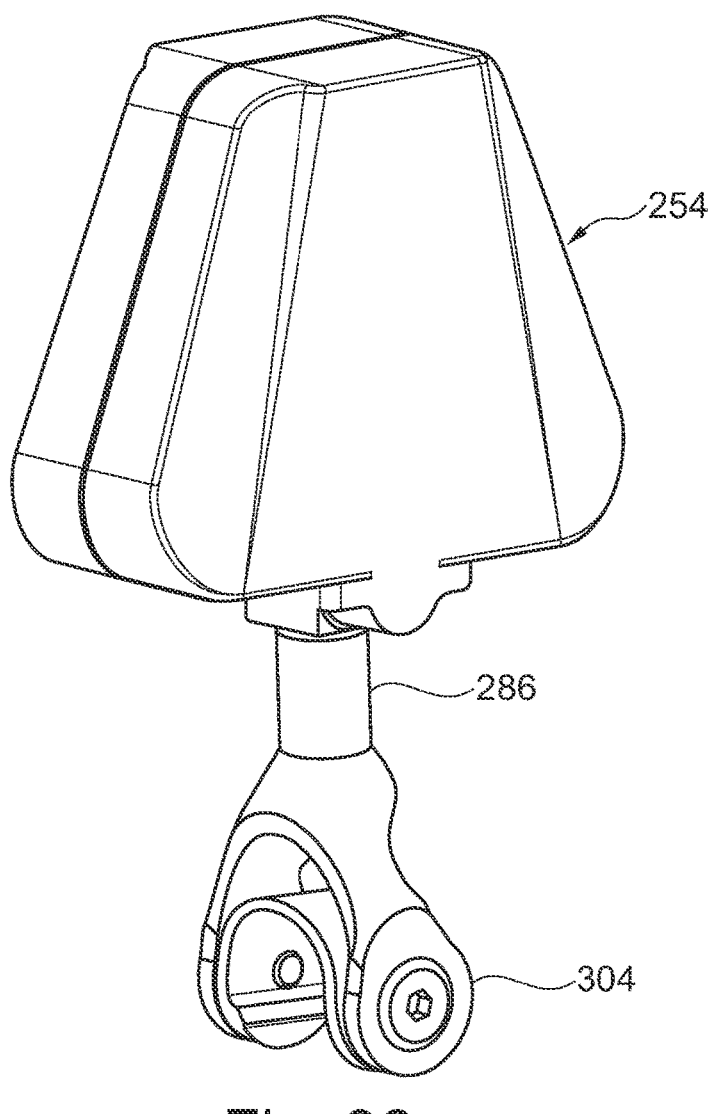
FIG. 36: an illustration of the central crank.

Nevertheless, the correspondence of the central crank module 254 ends at the crank arm 286, which integrates a universal joint 304 for the fixation of the manipulator arm 250, as is illustrated in FIG. 36.

In contrast with the crank modules 122 for the struts 124, balancing of the crank 286 is not desired for the central crank module 254, as this would nearly double the moving mass of the manipulator arm 250.

Instead, the integration of a weight compensation mechanism is suggested to balance the central crank over its 60 degree stroke.

FIG. 37 and FIG. 38 illustrate the extreme orientations for the pitch (FIG. 37) and yaw axis (FIG. 38) respectively.

Both joints allow for an angular variation of 150 degrees, and when operated simultaneously they allow the instrument 106 to dexterously orient to the workspace.

On the contrary, the roll axis allows infinite rotation and can therefore assume any required orientation.

CONCLUSION

A novel concept design for a seven degree of freedom robotic arm/manipulator dedicated to assist microsurgeons in small-scale anastomoses is proposed. This medical robot sets out to provide superhuman operating precision to facilitate the fine manipulations essential in achieving high quality anastomosis.

The concept is build on the identification and reevaluation of user requirements to tailor the solution to the field of microsurgery.

Manual access to the operating site and a direct line of view both through and underneath the microscope are preserved. From user preferences and procedural conveniences, high instrument dexterity and direct control are identified high potential aspects to improve the precision and efficiency of fine manipulations. The proposed design for the seven degree of freedom robotic system is composed of a three degree of freedom structure for the positioning of the manipulator arm; a three degree of freedom serial spherical wrist to orient the instrument; and a seventh degree of freedom to operate grasp at the instrument beaks.

Moreover, this instrument is designed a custom variant of the needle holder, that is compactly integrated into the manipulator and may be interchanged during the procedure. It allows any of the microsurgical needles to be grasped with over 5 N of clamping force, while the beaks fully close within one second, symmetrically from a maximum spread of 2 mm at the tip. In addition, both instrument pitch and yaw may be operated over an angular stroke of up to 150 degrees, while instrument roll is unbounded and hence allows for infinite rotation.

Moreover, the grasp, roll, pitch, and yaw drives are all designed sterilizable. In particular, the instrument module, the pitch module and/or the yaw module and/or the crank module comprise joints for orienting the instrument and/or instrument grasp, wherein these joints are configured sterilizable.

This allows the drape to be situated further from the instrument such that it causes minimal interference and visual obstruction.

Three crank-modules serve to precisely control the manipulator arm, where the slender struts act close to the center of the wrist for direct control over the instrument position. These cranks are operated in direct drive for high precision, although the central crank requires an additional mechanism to be designed for weight compensation.

For safety, the yaw orientation and instrument position are fully backdrivable to allow manual repositioning upon fault or convenience. In addition, the manipulator arm and strut cranks are balanced such that the system does not collapse on loss of power.

In addition, all but the grasp and roll drive integrate a redundant pair of absolute position sensors for fault detection. These also serve to provide instantaneous awareness of the manipulator configuration on startup without requiring a homing procedure.

In contrast, for grasp and roll no position sensors are implemented as these drives are argued safe in open-loop control.

In addition, sterile barriers are implemented exclusively in configurations where the seal may bond rigidly to the respective components, without relative motion between mating surfaces. These local seals and the drape together significantly reduce the number of components directly exposed to autoclave conditions and thereby allow more compact and precise drives to be constructed. For efficiency in cleaning and sterilization the slave manipulator is designed to easily disassemble and thereby improves exposure of the submodule surfaces.

REFERENCES 100 robotic arm
102 instrument module
104 instrument actuation submodule
106 instrument, forceps, needle holder
108 motor for actuation of roll
110 drivetrain for actuation of roll
112 motor for actuation of grasp
114 drivetrain for actuation of grasp
116 pitch module/yaw shaft
118 yaw module
120 instrument position module
122 crank module
124 strut
126 instrument submodule
128 drape
130 pitch axis
132 yaw axis
134 roll axis
136 quick lock clip
138 instrument retainer
140 retainer shell
142 instrument beak
144 instrument hinge pin
146 instrument handle
148 handle joint
150 retainer guide pin
152 knee linkage
154 stopper
156 knee mechanism central joint
158 pushrod
160 preload band
162 preload band guide pulley
163 instrument guide
164 roll drive actuator/motor
166 roll drivetrain
168 grasp drive actuator/motor
170 grasp drivetrain
172 drive gear
174 motor pinion
176 pushrod guide
178 leadscrew nut
180 preload nut
182 bearing spacer
184 miniature bearing
186 compliant seal
187 internal gear
188 roll external gear
190 bellow
192 excenter shaft
194 ball bearings
196 motor pinion
198 balance mass
200 pitch module
202 pitch drive mechanism
204 flat cable
206 actuator/motor plus absolute encoder
208 plain bearing
210 pitch belt 212 forked pull member
214 bellow type compliant seal
216 pitch module enclosure
218 assembly guide bushing
220 communication interface
222 yaw sensor magnet
224 linear ball bearing
226 non-locating ball bearing
228 ball screw
230 ball screw nut retainer
232 sensor scale
234 ball screw locknut
236 preload spring
238 stopper
240 pull member
242 absolute linear position sensor
244 locating bearing support
246 torsion stiff coupling
248 yaw module
250 manipulator arm
252 strut
254 (central) crank module
256 yaw rotor submodule
258 rotor (magnet)
260 inductive encoder rotor face
262 protective shell
264 hollow shaft
266 anti-loss nut
268 sensor submodule
270 inner tube, yaw shaft
272 outer tube
274 universal joint
276 radial connector segment
278 spiral flat cable
280 connector
282 crank arm bearing
284 base frame
286 crank, crank arm
288 motor/rotor coil
290 encoder scale
292 spherical/ball joint
294 band
296 surgical tape
298 arc segment
300 coil support structure
302 spherical end-stop
304 universal joint
306 needle

The invention claimed is:

1. A robotic arm for use in surgery, microsurgery or supermicrosurgery, comprising:
at least one instrument module comprising an instrument actuation submodule; wherein the instrument is a needle holder and/or forceps for surgery, microsurgery or supermicrosurgery, comprising two instrument beaks, at least one instrument hinge pin, at least two instrument handles and at least two handle joints,
wherein the instrument actuation submodule is configured to operate grasp and roll orientation of an instrument,
wherein the instrument actuation submodule comprises a first motor and a first drivetrain for actuation of the instrument roll orientation,
wherein the instrument actuation submodule comprises a second motor and a second drivetrain for actuation of the instrument grasp orientation,
at least one pitch module, and
at least one yaw module, wherein the first motor and the second motor are integrated into the instrument actuation submodule side-by-side for compactness.

2. The robotic arm according to claim 1, wherein first drivetrain of the instrument actuation submodule is configured and arranged for infinite instrument rotation.

3. The robotic arm according to claim 1, wherein the at least one pitch module comprises a pitch drive mechanism configured and arranged to actuate instrument pitch over an angular stroke of up to 150 degrees.

4. The robotic arm according to claim 1, wherein the at least one yaw module comprises a yaw drive mechanism configured and arranged to actuate instrument yaw over an angular stroke of up to 150 degrees.

5. The robotic arm according to claim 1, wherein the instrument module further comprises an instrument submodule, the instrument submodule comprising an instrument retainer and the instrument.

6. The robotic arm according to claim 5, wherein the robotic arm further comprises at least one instrument position module comprising at least three crank modules, wherein at least two of the crank modules are each linked to at least one strut.

7. The robotic arm according to claim 6, wherein at least two of the crank modules are linked to the same strut.

8. The robotic arm according to claim 6, wherein the robotic arm is a seven degree of freedom robotic arm, wherein the instrument actuation submodule is a three degree of freedom module, the instrument submodule is a one degree of freedom module and the at least one instrument position module is a three degree of freedom module.

9. The robotic arm according to claim 6, wherein the instrument module, the at least one pitch module and/or the at least one yaw module and/or one of the crank modules comprise joints for orienting the instrument and/or instrument grasp, wherein these joints are configured sterilizable.

10. The robotic arm according to claim 5, wherein the instrument retainer further comprises at least one instrument preload band and at least one preload band guide pulley.

11. The robotic arm according to claim 1, wherein the robotic arm comprises at least one parallel kinematic structure being formed by at least one of the at least one instrument module and/or the at least one yaw module and/or the at least one pitch module and/or at least one instrument position module.

12. The robotic arm according to claim 1, wherein the instrument has a length of less than 50 mm.

13. The robotic arm according to claim 1, wherein the two instrument beaks each have a length of less than 20 mm.

14. A robotic system for use in surgery, microsurgery or supermicrosurgery, comprising at least two robotic arms according to claim 1.

15. The robotic arm according to claim 1, wherein the surgery, microsurgery, or supermicrosurgery includes anastomosis.

16. A robotic arm for use in surgery, microsurgery or supermicrosurgery, comprising:
an instrument module comprising:
an instrument actuation submodule configured to operate grasp and roll orientation of an instrument, and
an instrument submodule comprising an instrument retainer and the instrument;
wherein the instrument is configured and arranged for an inverted hinge mechanism.

17. The robotic arm according to claim 16, wherein the instrument retainer comprises at least one knee mechanism central joint, at least two retainer guide pins, at least one stopper, at least one knee link pair, wherein the instrument retainer is configured to actuate the instrument via the inverted hinge mechanism.

18. The robotic arm according to claim 17, wherein the instrument actuation submodule comprises a pushrod configured and arranged for actuating over a centerline of the instrument actuation submodule.

19. The robotic arm according to claim 18, wherein the pushrod comprises a spherical tip configured for contacting a matching socket in the at least one knee mechanism central joint.

* * * * *